(12) United States Patent
Mendels et al.

(10) Patent No.: US 9,357,950 B2
(45) Date of Patent: Jun. 7, 2016

(54) APPARATUS AND METHOD OF FLUID ASPIRATION

(75) Inventors: Yair Mendels, Moza Elit (IL); Elad Uziel, Kadish Luz (IL); Shamir Matan, Jerusalem (IL); Ilya Revzin, Jerusalem (IL); Eldad Gabriel Rubinstein, Jerusalem (IL); Vered Aframian, Jerusalem (IL); Yehonatan Gershuni, Jerusalem (IL); Orga Marco, Yad Hshmona (IL)

(73) Assignee: BIOMETRIX LTD., Jerusalem (IL)

( * ) Notice: Subject to any disclaimer, the term of this patent is extended or adjusted under 35 U.S.C. 154(b) by 1185 days.

(21) Appl. No.: 13/296,327

(22) Filed: Nov. 15, 2011

(65) Prior Publication Data

US 2012/0123298 A1    May 17, 2012

Related U.S. Application Data

(63) Continuation-in-part of application No. PCT/US2010/037043, filed on Jun. 2, 2010.

(60) Provisional application No. 61/183,886, filed on Jun. 3, 2009, provisional application No. 61/414,427, filed on Nov. 17, 2010.

(51) Int. Cl.
*A61B 5/15* (2006.01)
*A61B 5/00* (2006.01)
(Continued)

(52) U.S. Cl.
CPC ........... *A61B 5/1427* (2013.01); *A61B 5/15003* (2013.01); *A61B 5/153* (2013.01);
(Continued)

(58) Field of Classification Search
CPC ........... A61B 5/1427; A61B 5/150992; A61B 5/150244; A61B 5/150251; A61B 5/1416; A61M 2005/3152; A61M 5/31596; A61M 5/3148; A61M 5/1452; A61M 5/16854
See application file for complete search history.

(56) References Cited

U.S. PATENT DOCUMENTS 3,957,082 A    5/1976  Larson et al.
4,177,835 A   12/1979  Paley
(Continued)

FOREIGN PATENT DOCUMENTS

DE    3544676    7/1986
EP    0242128   10/1987
(Continued)

OTHER PUBLICATIONS

International Search Report dated Jan. 10, 2011 for PCT/US10/37043.
(Continued)

*Primary Examiner* — Sean Dougherty
*Assistant Examiner* — Megan Leedy
(74) *Attorney, Agent, or Firm* — Paul D. Bianco; Fleit Gibbons Gutman Bongini & Bianco PL

(57) ABSTRACT

An in-line sampling system that includes a sampling valve and a syringe for selectively introducing a fluid to and aspirating a fluid from a downstream fluid conduit connected to a catheterized patient. The syringe has a fluid chamber into which fluid is aspirated, a volume regulator for adjusting the volume, a fluid line through which fluid flows through the syringe to a downstream fluid conduit. The syringe also has a valve mechanism for selectively controlling fluid flow along the fluid line and selectively shifting the volume regulator to adjust the volume of the fluid chamber. A housing provides for the fluid chamber and mounts the fluid line, valve mechanism and volume regulator.

17 Claims, 28 Drawing Sheets

(51) Int. Cl.

| | |
|---|---|
| *A61M 5/00* | (2006.01) |
| *A61B 5/155* | (2006.01) |
| *A61B 5/153* | (2006.01) |
| *G06F 19/00* | (2011.01) |
| *A61M 5/145* | (2006.01) |
| *A61M 39/22* | (2006.01) |
| *A61M 39/00* | (2006.01) |

(52) U.S. Cl.
CPC .......... *A61B 5/155* (2013.01); *A61B 5/150213* (2013.01); *A61B 5/150221* (2013.01); *A61B 5/150229* (2013.01); *A61B 5/150236* (2013.01); *A61B 5/150862* (2013.01); *A61B 5/150946* (2013.01); *A61B 5/150992* (2013.01); *A61M 5/1452* (2013.01); *G06F 19/3468* (2013.01); *A61M 39/223* (2013.01); *A61M 2005/14533* (2013.01); *A61M 2039/0009* (2013.01); *A61M 2039/0018* (2013.01); *A61M 2206/11* (2013.01)

(56) References Cited

U.S. PATENT DOCUMENTS

| | | | |
|---|---|---|---|
| 4,257,416 A | | 3/1981 | Prager |
| 4,317,455 A | | 3/1982 | Akhavi |
| 4,343,516 A | | 8/1982 | Aden |
| 4,370,987 A | | 2/1983 | Bazell et al. |
| 4,432,392 A | | 2/1984 | Paley |
| 4,448,205 A | | 5/1984 | Stenkvist |
| 4,658,834 A | | 4/1987 | Blankenship et al. |
| 4,673,386 A | | 6/1987 | Gordon |
| 4,744,955 A | | 5/1988 | Shapiro |
| 4,745,929 A | | 5/1988 | Silver |
| 4,838,855 A | | 6/1989 | Lynn |
| 4,865,583 A | | 9/1989 | Tu |
| 4,936,315 A | | 6/1990 | Lineback |
| 5,048,537 A | * | 9/1991 | Messinger ............... 600/486 |
| 5,190,525 A | | 3/1993 | Oswald |
| 5,192,269 A | | 3/1993 | Poli et al. |
| 5,207,645 A | | 5/1993 | Ross et al. |
| 5,217,432 A | | 6/1993 | Rudzena et al. |
| 5,250,040 A | | 10/1993 | Parks et al. |
| 5,265,621 A | | 11/1993 | Simpson et al. |
| 5,277,198 A | | 1/1994 | Kanner et al. |
| 5,324,266 A | | 6/1994 | Ambrisco et al. |
| 5,374,248 A | | 12/1994 | Lopez |
| 5,374,401 A | | 12/1994 | von Berg |
| 5,431,185 A | | 7/1995 | Shannon et al. |
| 5,468,233 A | * | 11/1995 | Schraga ............... 604/207 |
| 5,486,159 A | | 1/1996 | Mahurkar |
| 5,527,299 A | | 6/1996 | Cude |
| 5,549,569 A | | 8/1996 | Lynn et al. |
| 5,666,966 A | | 9/1997 | Horie et al. |
| 5,699,821 A | | 12/1997 | Paradis |
| 5,738,662 A | | 4/1998 | Koenig |
| 5,758,643 A | | 6/1998 | Wong et al. |
| 5,759,160 A | | 6/1998 | Neese et al. |
| 5,769,087 A | | 6/1998 | Westphal et al. |
| 5,772,608 A | | 6/1998 | Dhas |
| 5,776,077 A | | 7/1998 | Kottig |
| 5,820,601 A | | 10/1998 | Mayer |
| 5,891,051 A | | 4/1999 | Han et al. |
| 5,961,472 A | | 10/1999 | Swendson et al. |
| 6,036,654 A | | 3/2000 | Siman et al. |
| 6,159,164 A | | 12/2000 | Neese et al. |
| 6,206,851 B1 | | 3/2001 | Prosel |
| 6,364,847 B1 | | 4/2002 | Shulze et al. |
| 6,364,861 B1 | | 4/2002 | Feith et al. |
| 6,406,458 B1 | | 6/2002 | Tillander |
| 6,428,520 B1 | | 8/2002 | Lopez et al. |
| 6,582,379 B1 | | 6/2003 | Stisen |
| 6,592,544 B1 | | 7/2003 | Currier et al. |
| 6,640,649 B1 | | 11/2003 | Paz et al. |
| 6,953,450 B2 | | 10/2005 | Baldwin et al. |
| 7,112,177 B2 | | 9/2006 | Christensen et al. |
| 7,223,253 B2 | | 5/2007 | Hogendijk |
| 7,396,348 B2 | | 7/2008 | Newton et al. |
| 7,563,243 B2 | | 7/2009 | Mendels |
| 7,608,042 B2 | | 10/2009 | Goldberger et al. |
| 7,618,412 B2 | | 11/2009 | Chernack |
| 7,680,042 B2 | | 3/2010 | Rambo et al. |
| 7,744,573 B2 | | 6/2010 | Gordon et al. |
| 8,034,021 B2 | | 10/2011 | Mendels |
| 2002/0161314 A1 | | 10/2002 | Sarajarvi |
| 2003/0135165 A1 | | 7/2003 | Chernack |
| 2004/0176703 A1 | | 9/2004 | Christensen et al. |
| 2005/0096627 A1 | | 5/2005 | Howard |
| 2005/0121103 A1 | | 6/2005 | Steigerwalt et al. |
| 2005/0267445 A1 | | 12/2005 | Mendels |
| 2006/0058702 A1 | | 3/2006 | Christensen et al. |
| 2006/0229531 A1 | * | 10/2006 | Goldberger et al. .......... 600/573 |
| 2007/0088282 A1 | * | 4/2007 | Ranalletta et al. ............ 604/184 |
| 2007/0255167 A1 | | 11/2007 | Christensen et al. |
| 2008/0033400 A1 | | 2/2008 | Holper |
| 2008/0200837 A1 | * | 8/2008 | Frazier et al. ................ 600/573 |
| 2008/0306424 A1 | * | 12/2008 | Gallogly et al. .............. 604/6.1 |
| 2010/0022967 A1 | | 1/2010 | Mendels |
| 2010/0137778 A1 | | 6/2010 | Kunjan et al. |
| 2010/0217154 A1 | | 8/2010 | Deshmukh et al. |
| 2011/0288494 A1 | | 11/2011 | Mendels |

FOREIGN PATENT DOCUMENTS

| | | |
|---|---|---|
| EP | 0901778 | 7/1998 |
| EP | 1749549 | 8/2005 |
| FR | 2358601 | 2/1978 |
| FR | 2513520 | 4/1983 |
| WO | 00/27452 | 5/2000 |
| WO | 2004/045704 | 3/2004 |
| WO | 2004-45704 | 6/2004 |
| WO | 2010141458 | 12/2010 |
| WO | 2010141563 | 12/2010 |

OTHER PUBLICATIONS

International Search Report published Dec. 23, 2004 for PCT/IL2003/00983, filed Nov. 19, 2003.
International Search Report published Feb. 7, 2011 for PCT/US2010/036887, filed Jun. 1, 2010.
International Search Report published Jan. 12, 2011 for PCT/US2010/037043, filed Jun. 2, 2010.
International Preliminary Report of Patentability dated Dec. 6, 2011 for PCT/US10/37043 filed Jun. 2, 2010.
International Preliminary Report of Patentability dated Dec. 6, 2011 for PCT/US10/36887 filed Jun. 1, 2010.

* cited by examiner

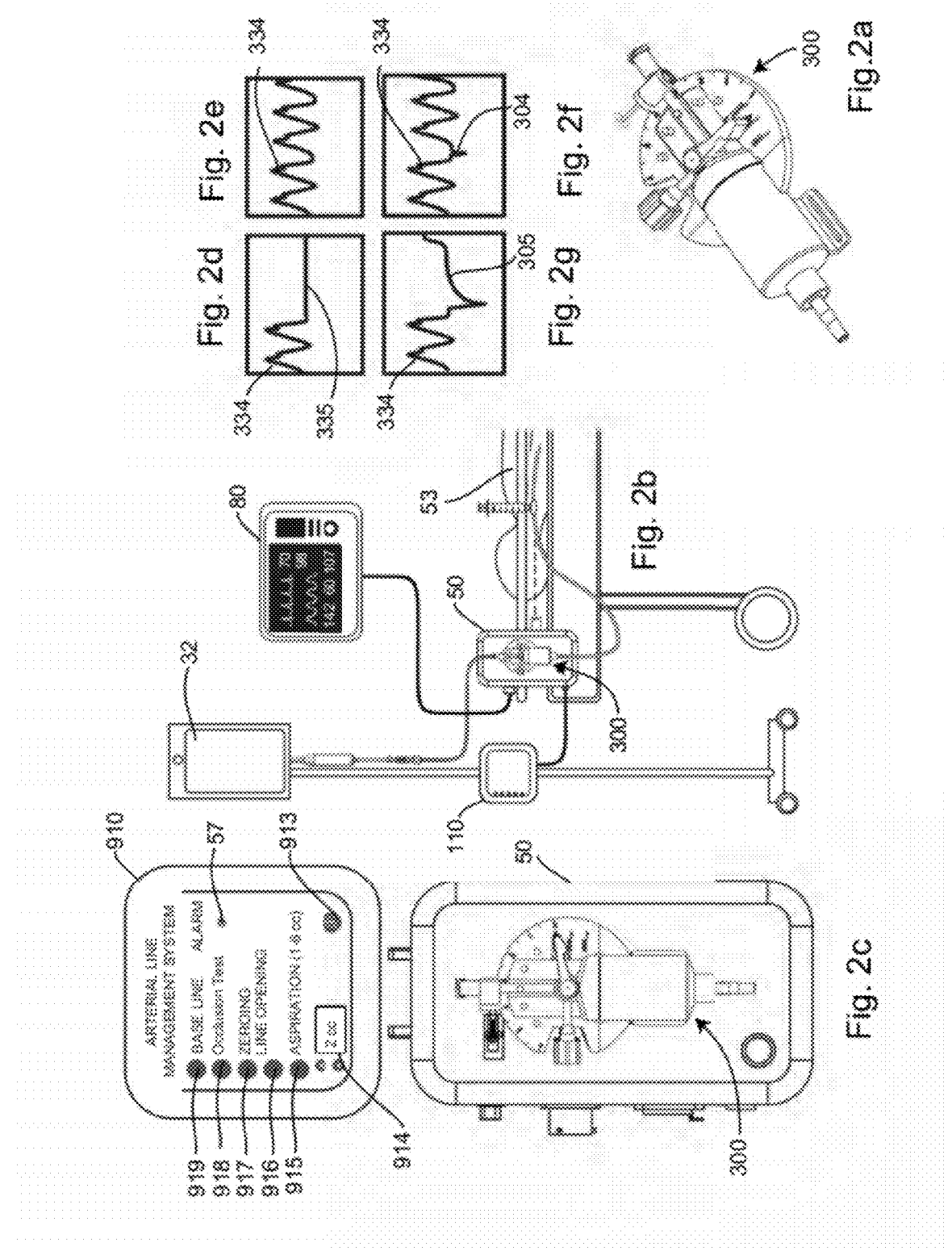

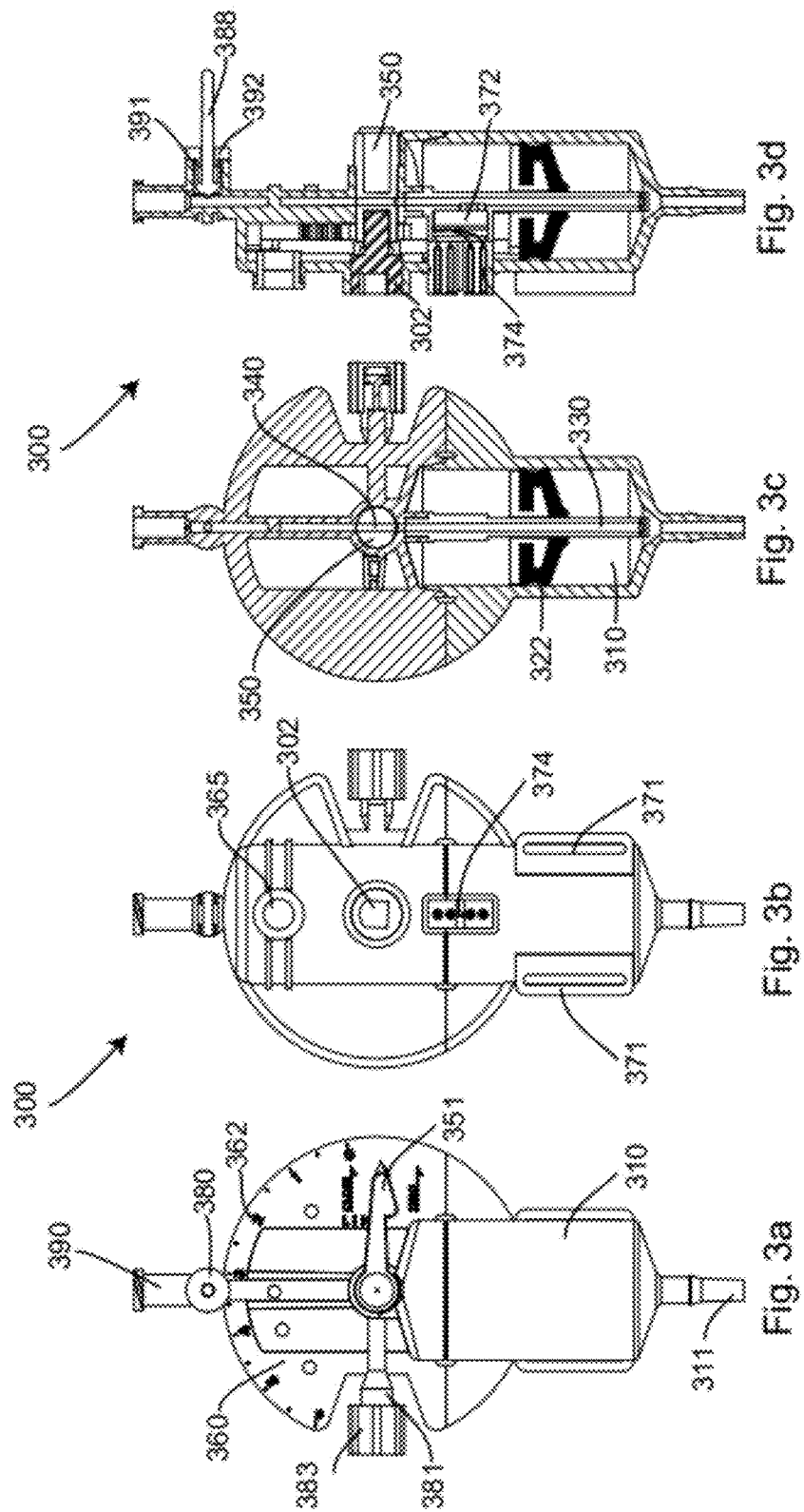

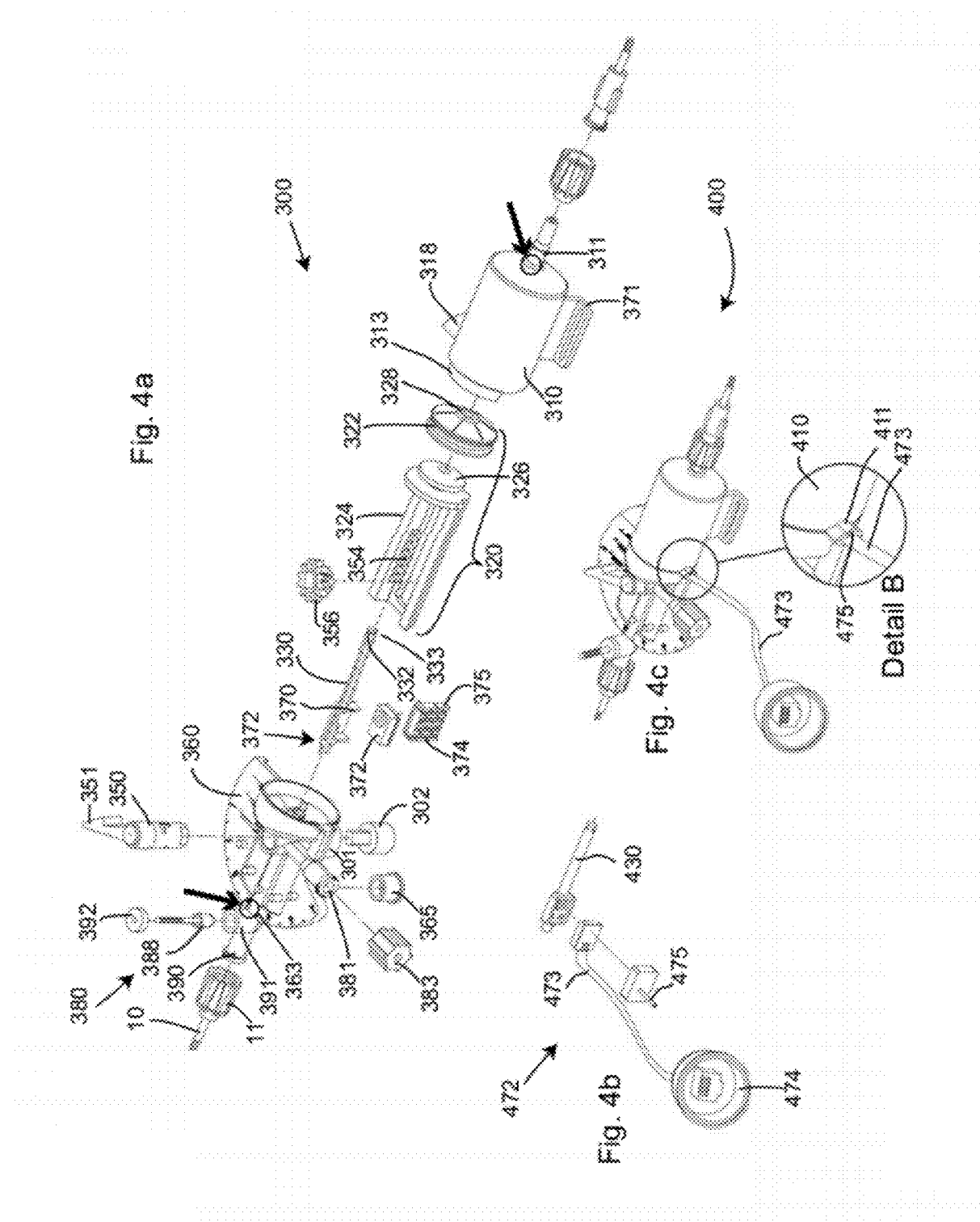

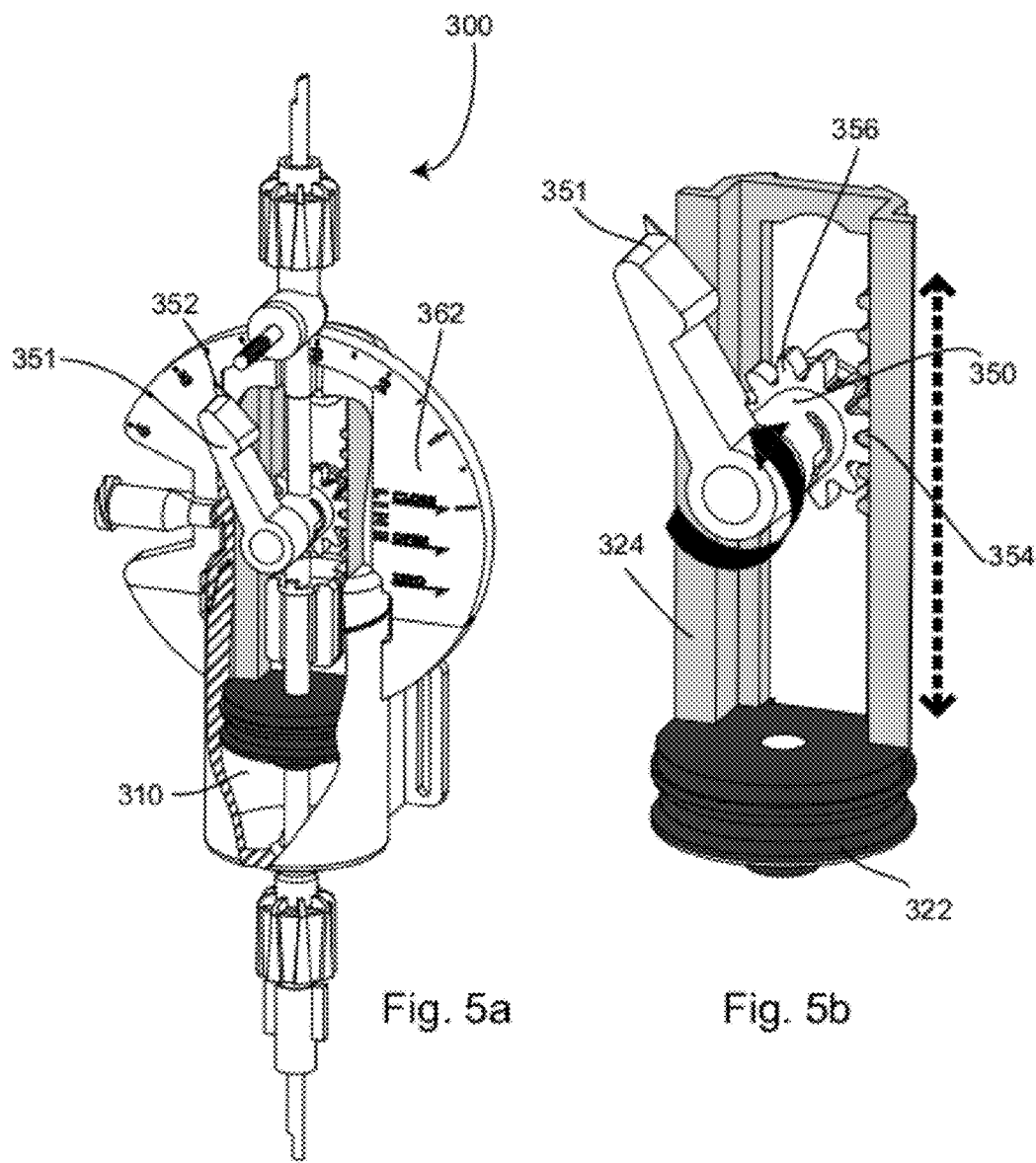

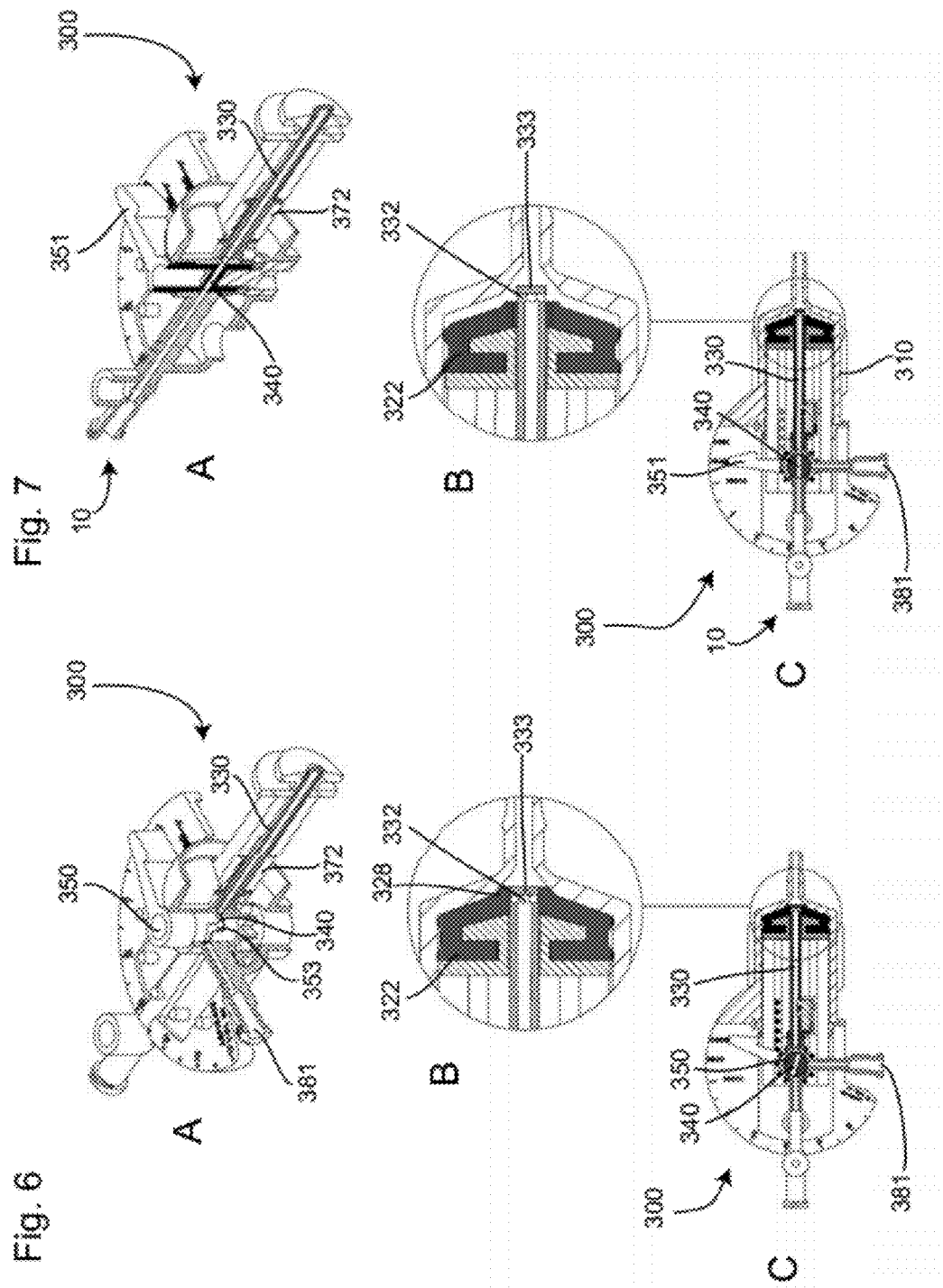

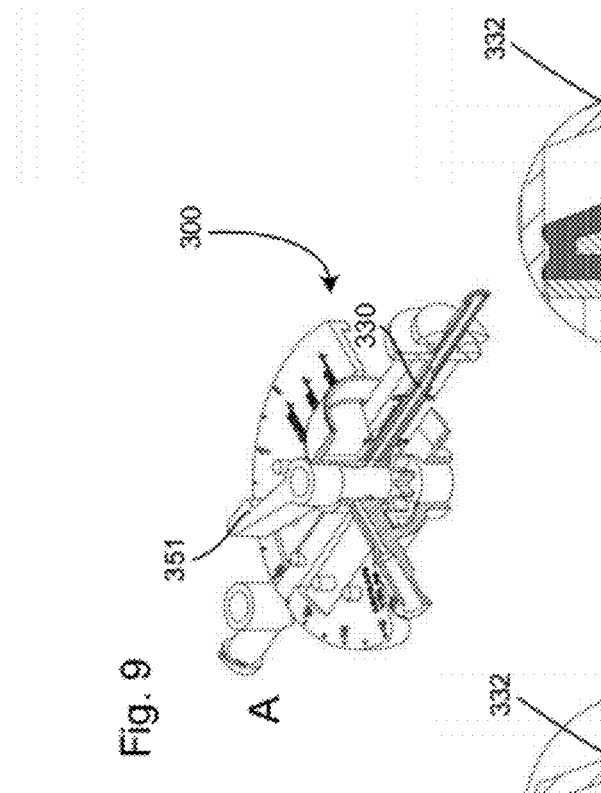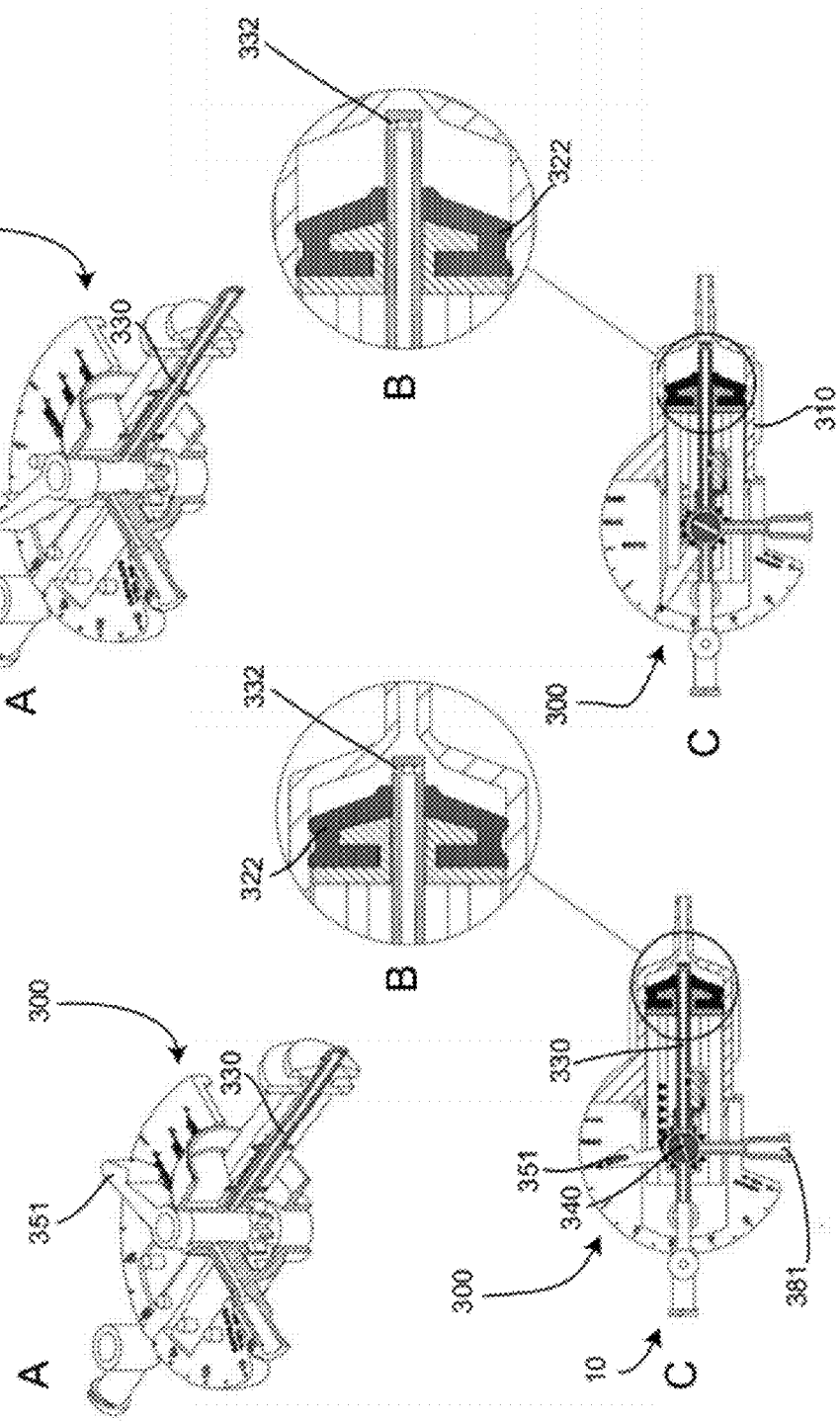

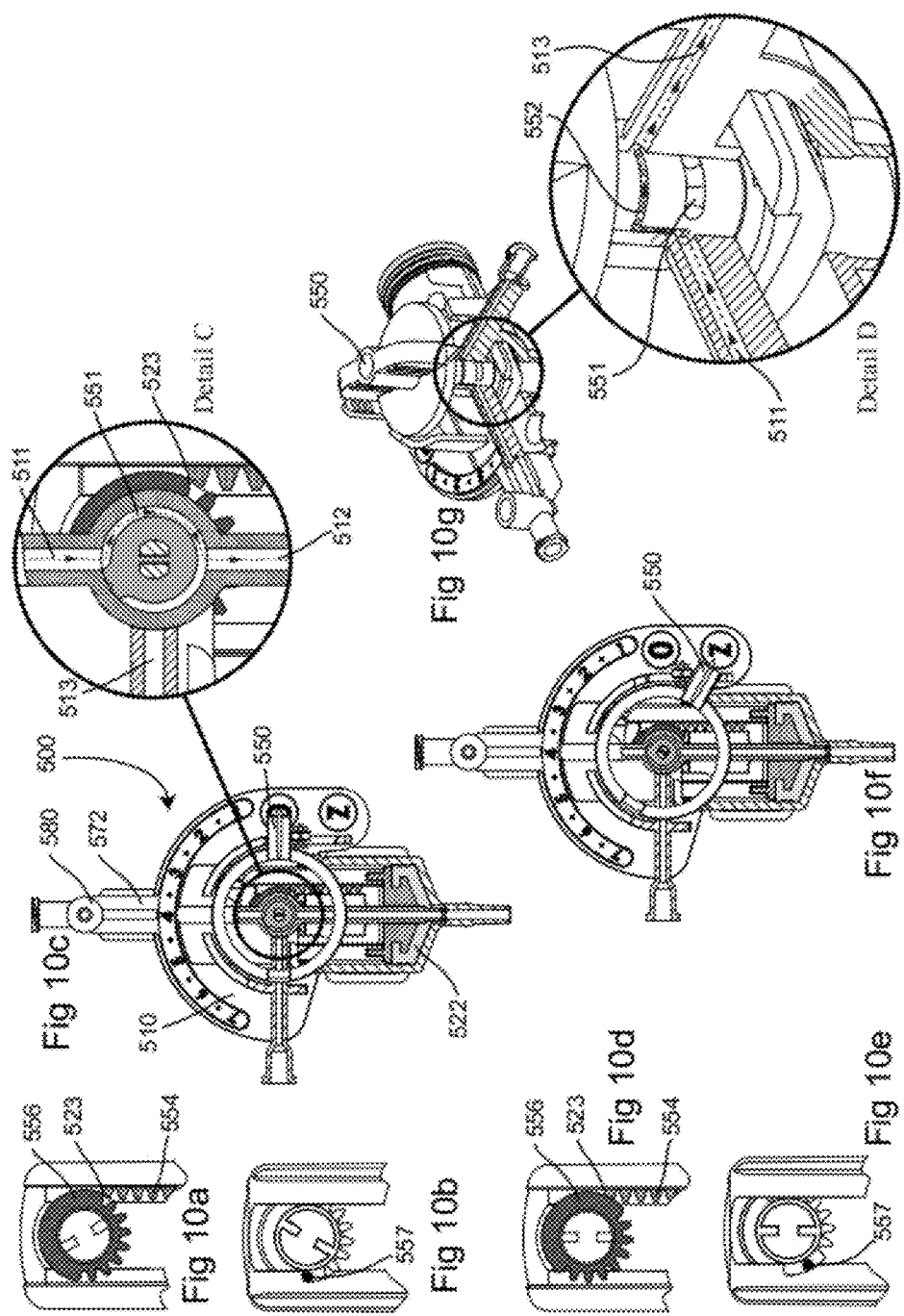

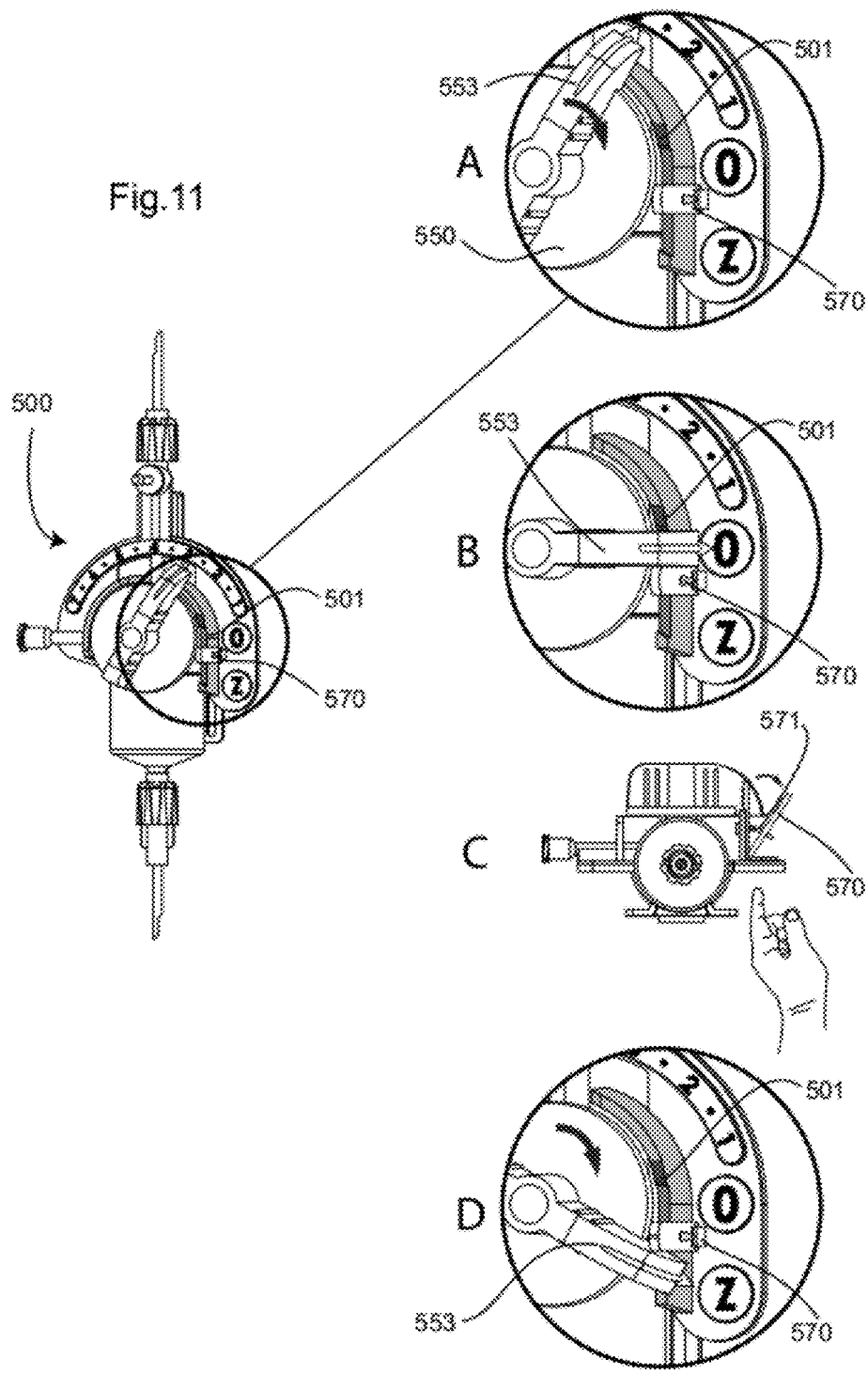

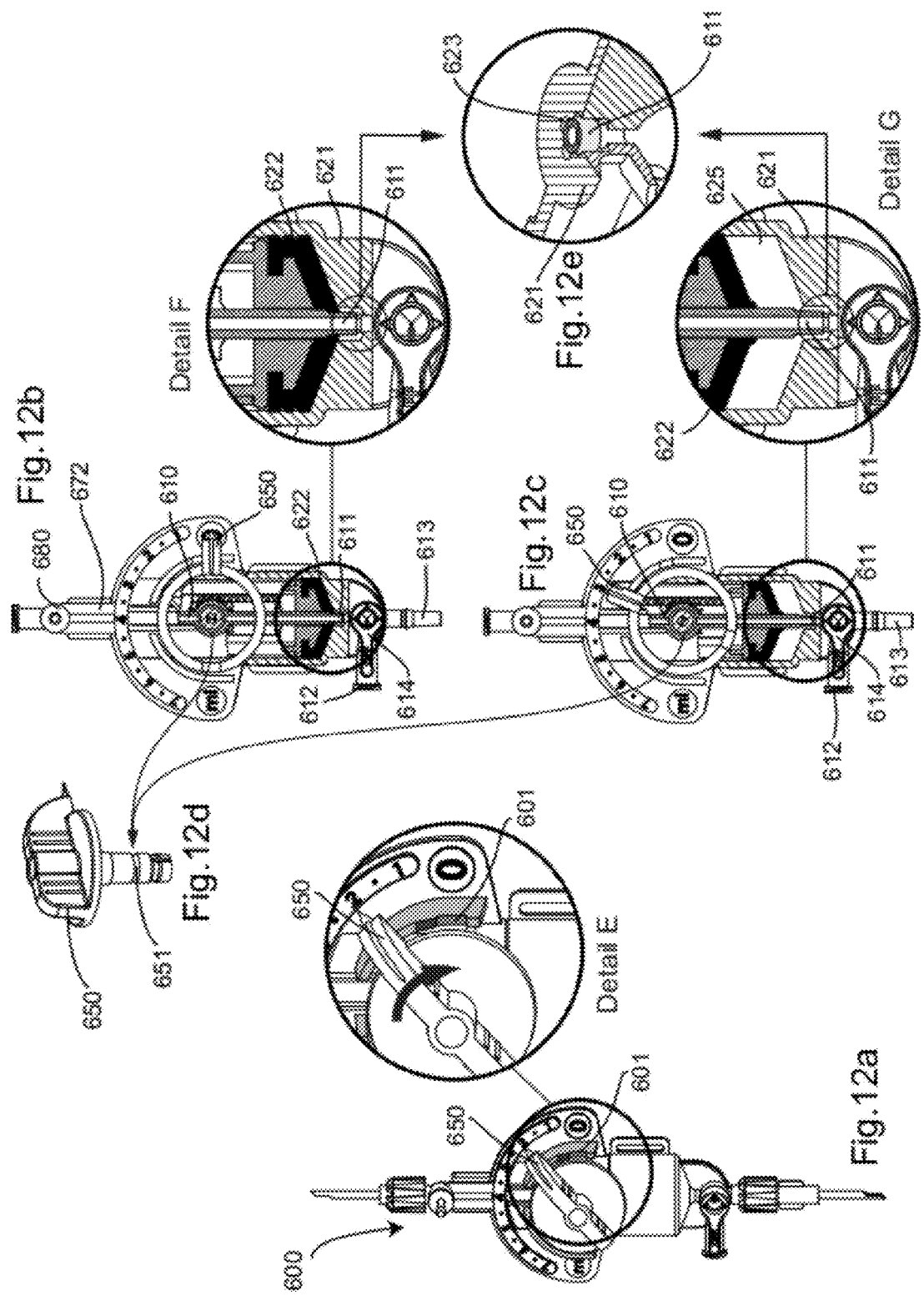

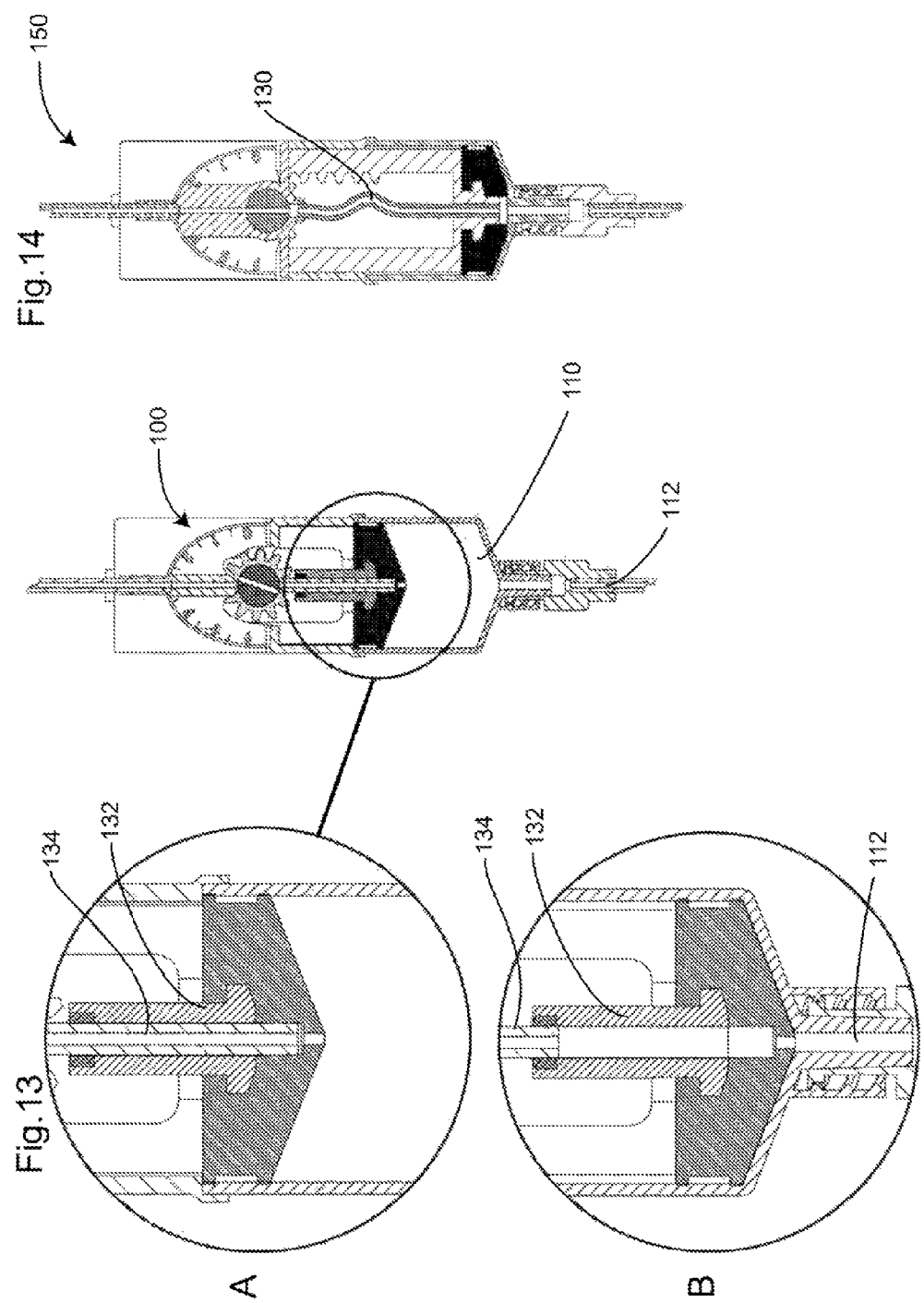

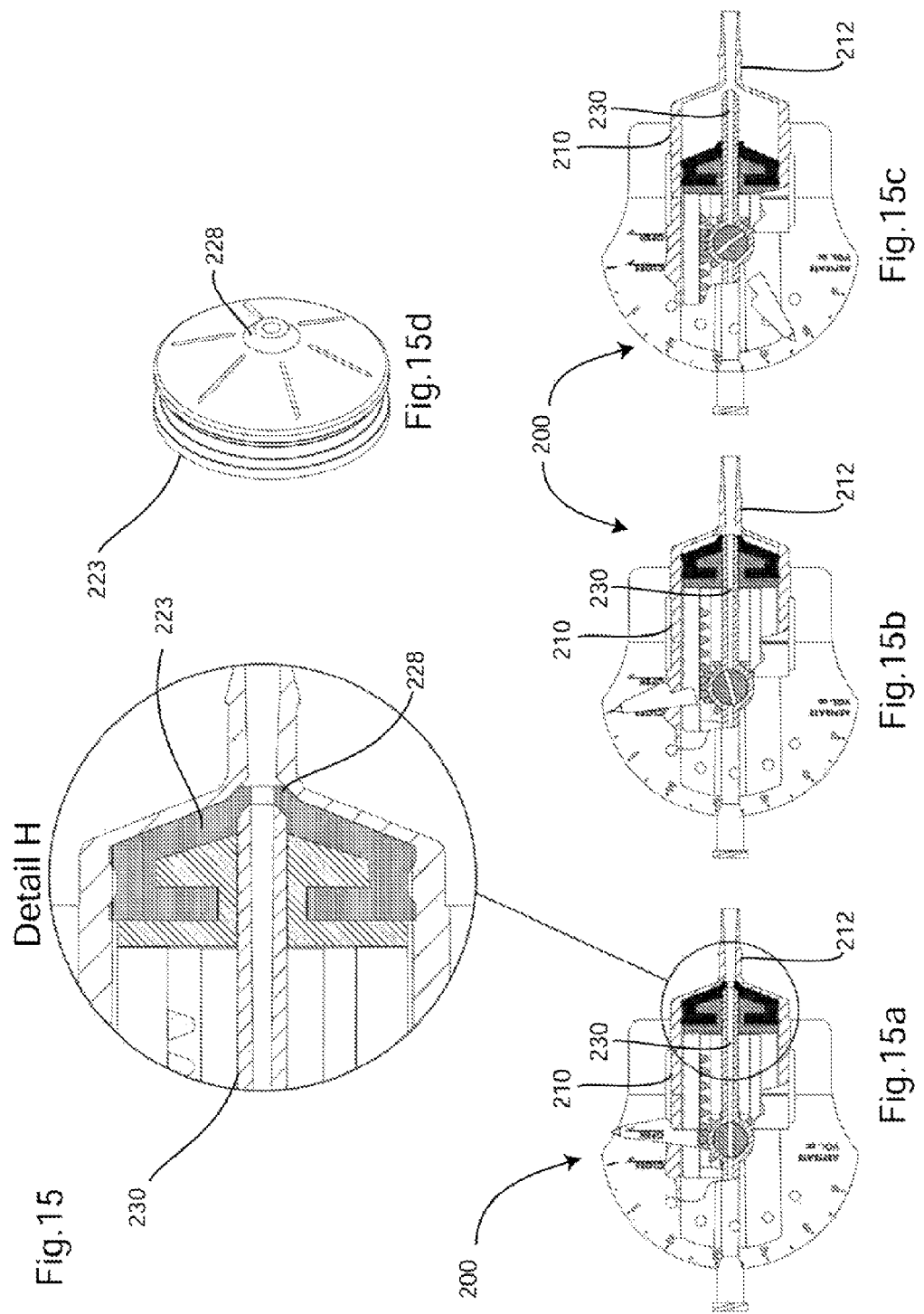

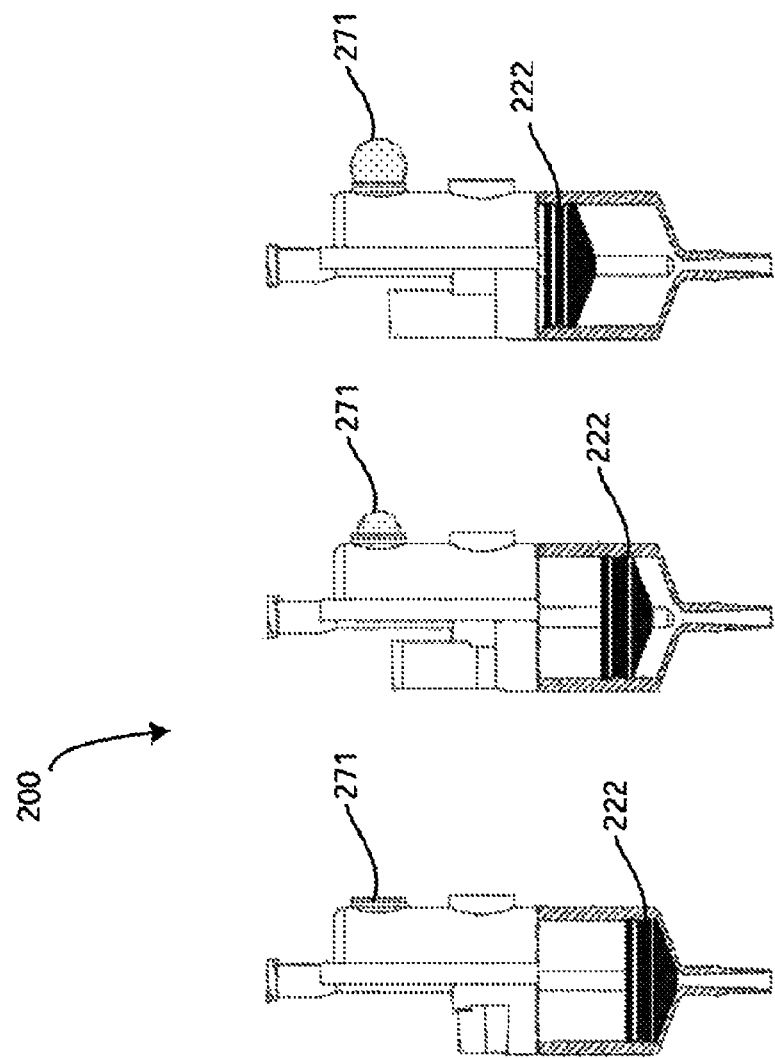

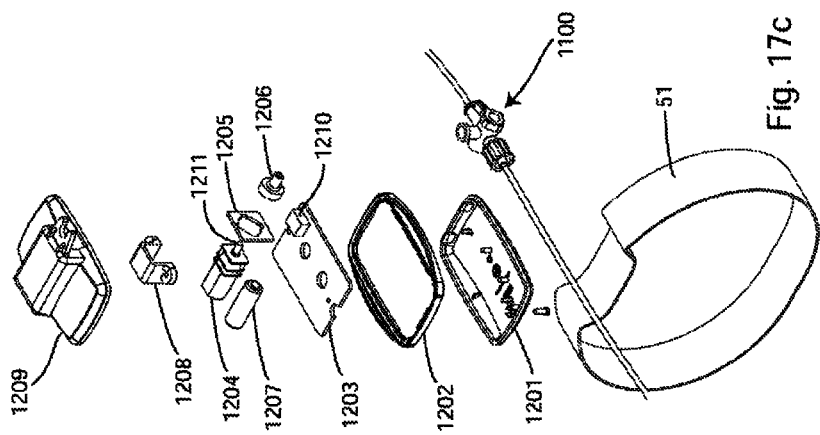
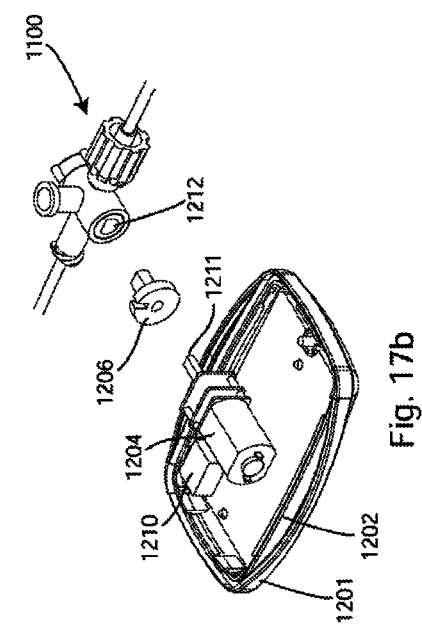
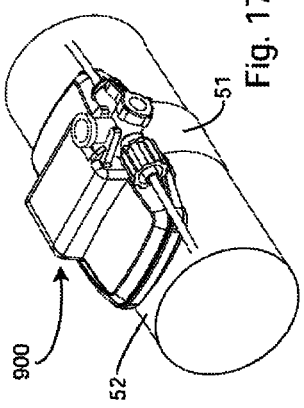

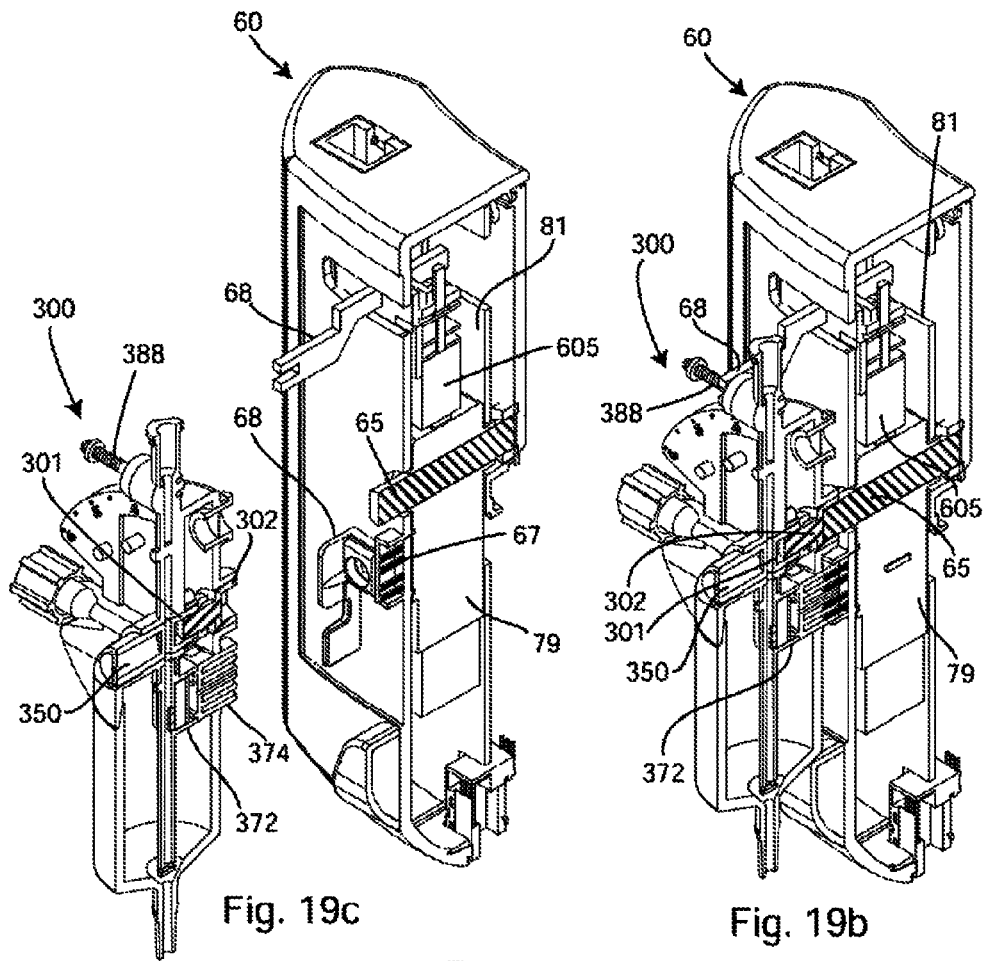
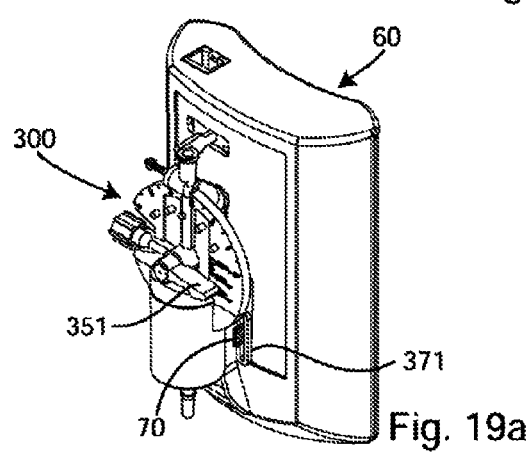
Fig. 19c
Fig. 19b
Fig. 19a

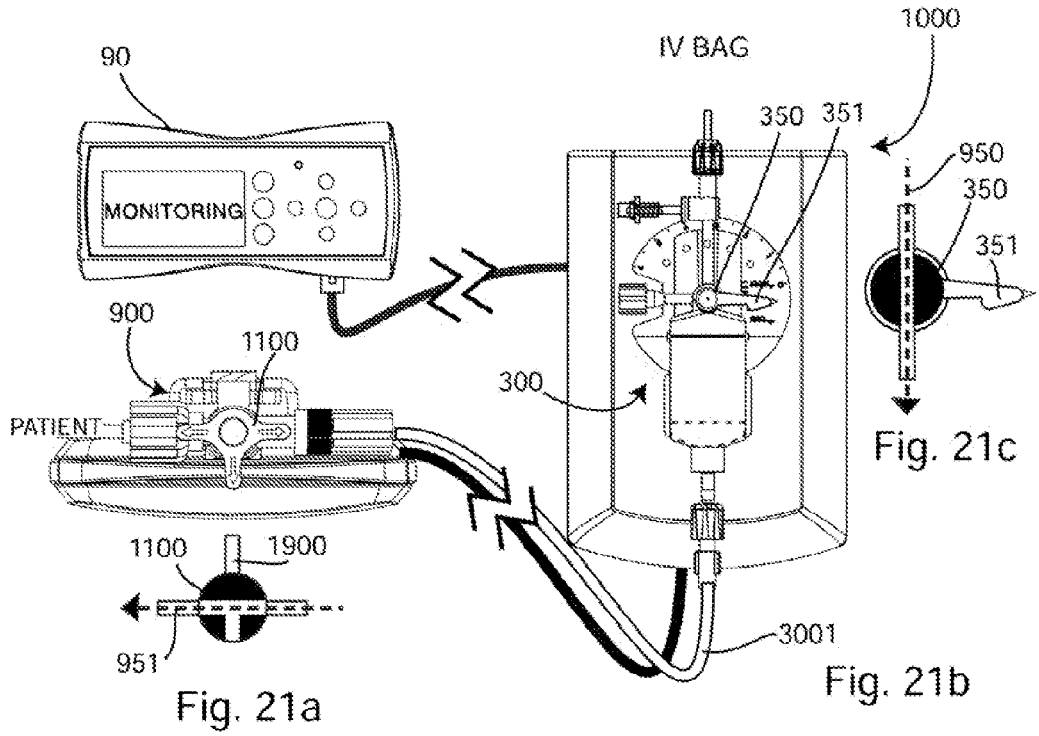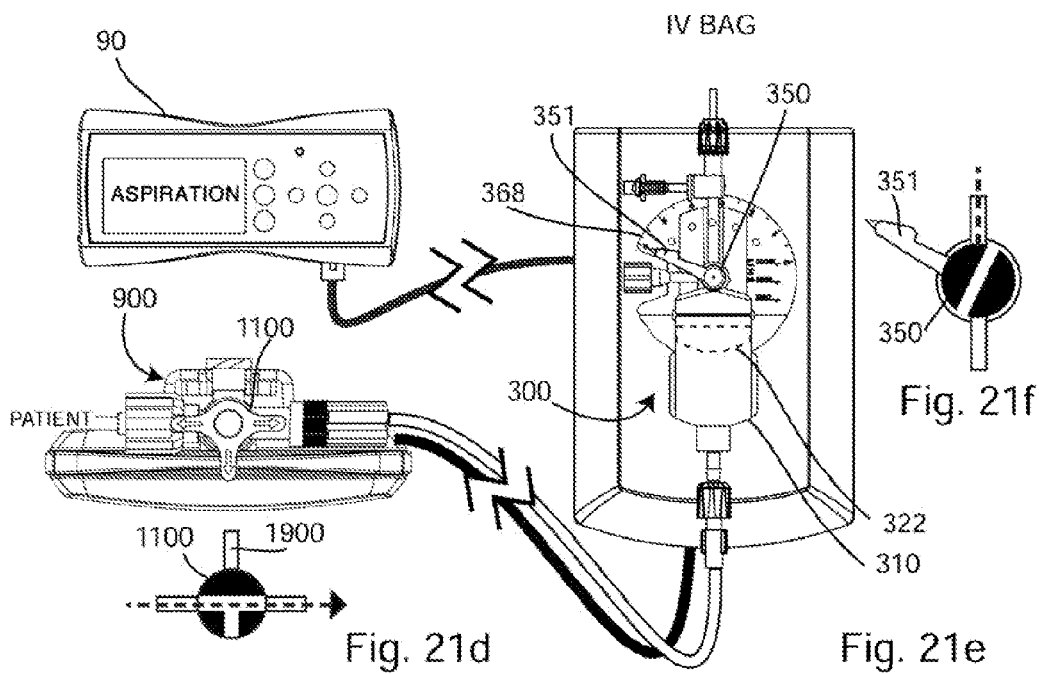

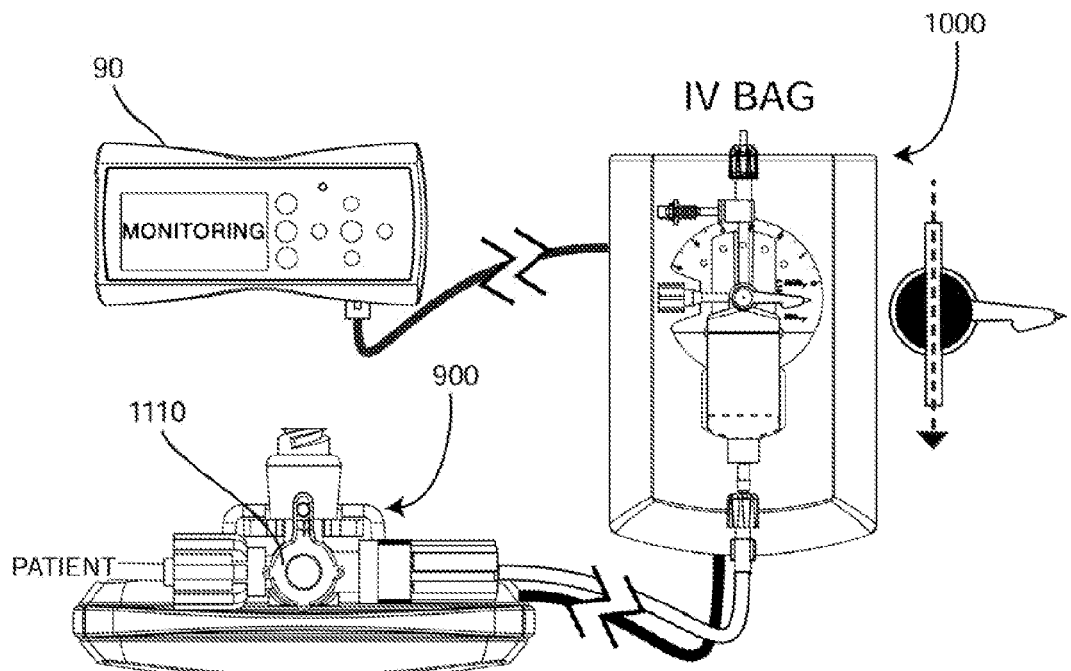
Fig. 22a
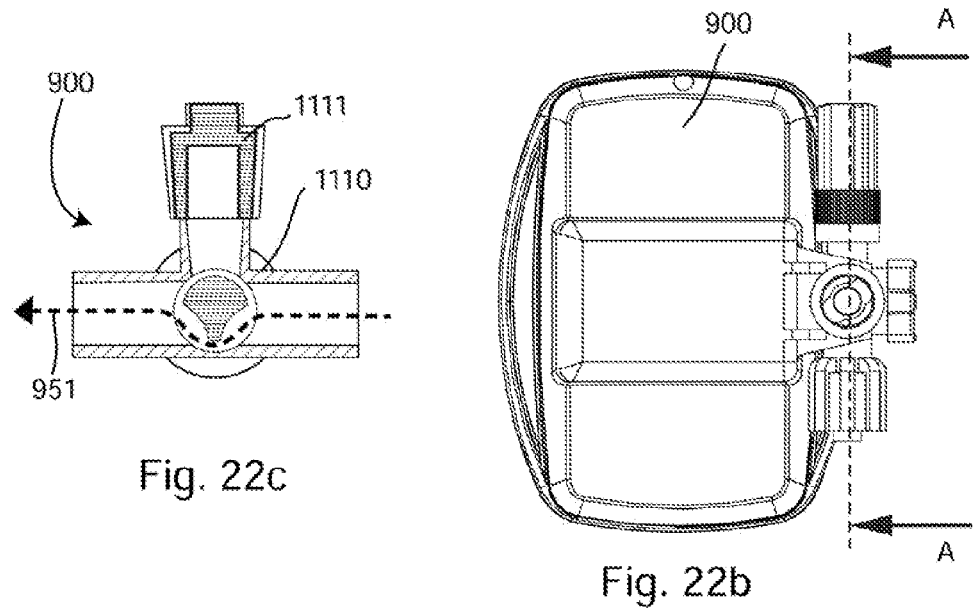
Fig. 22c
Fig. 22b

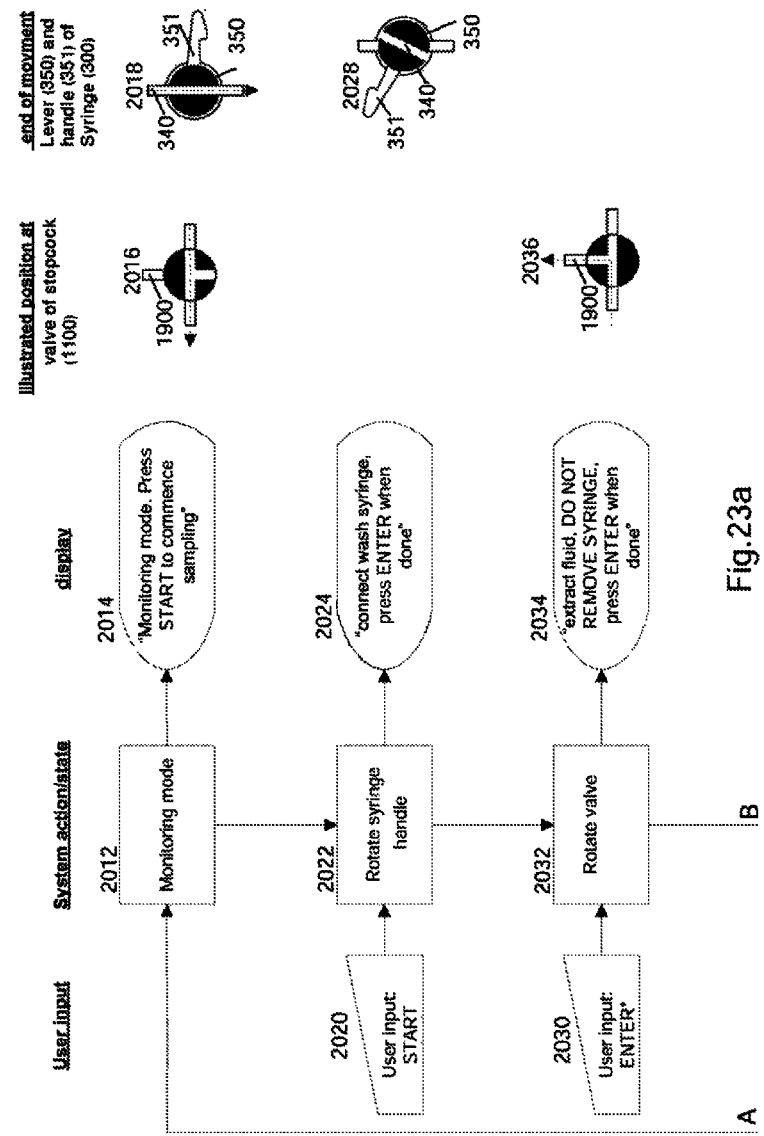

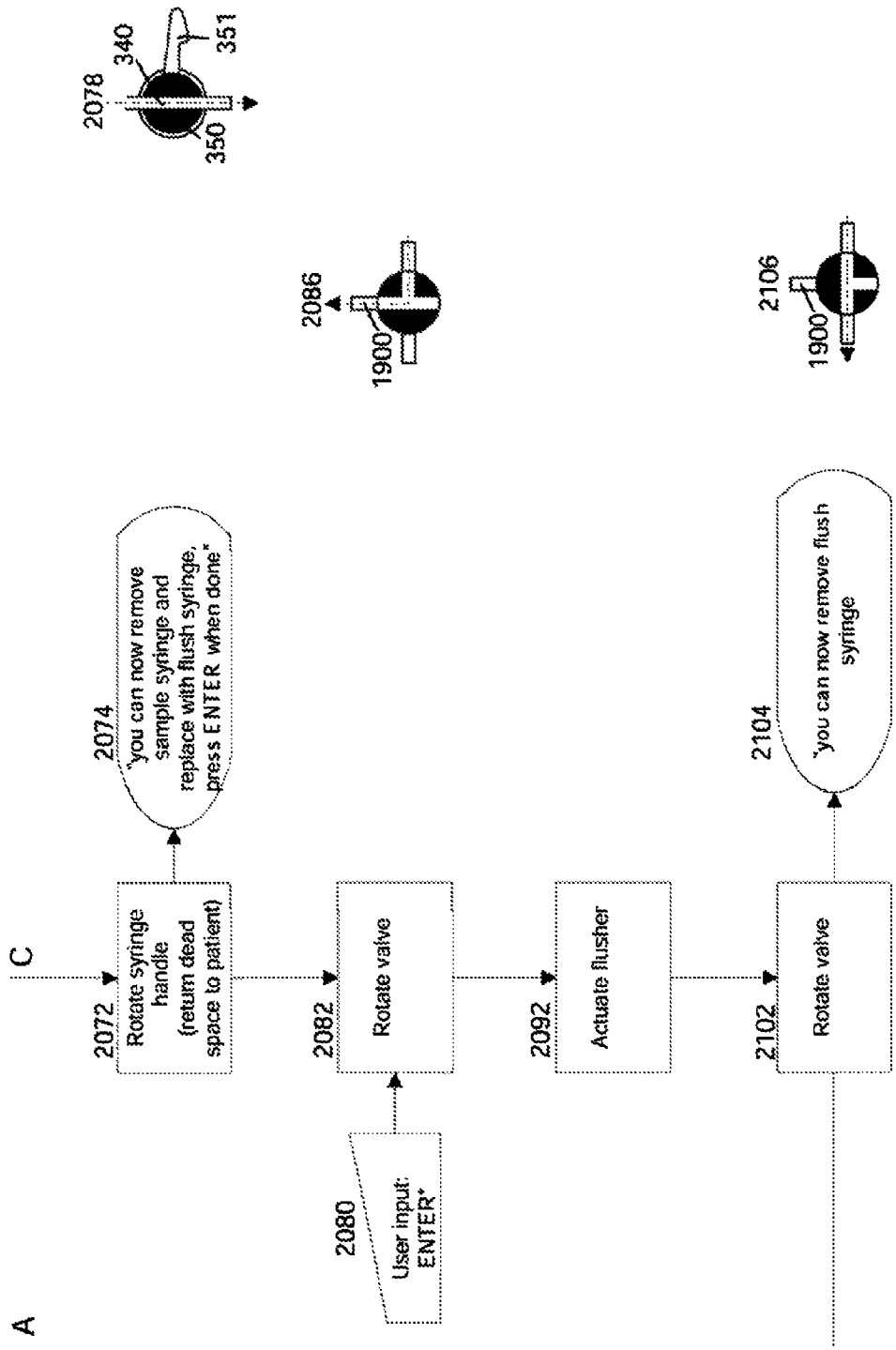

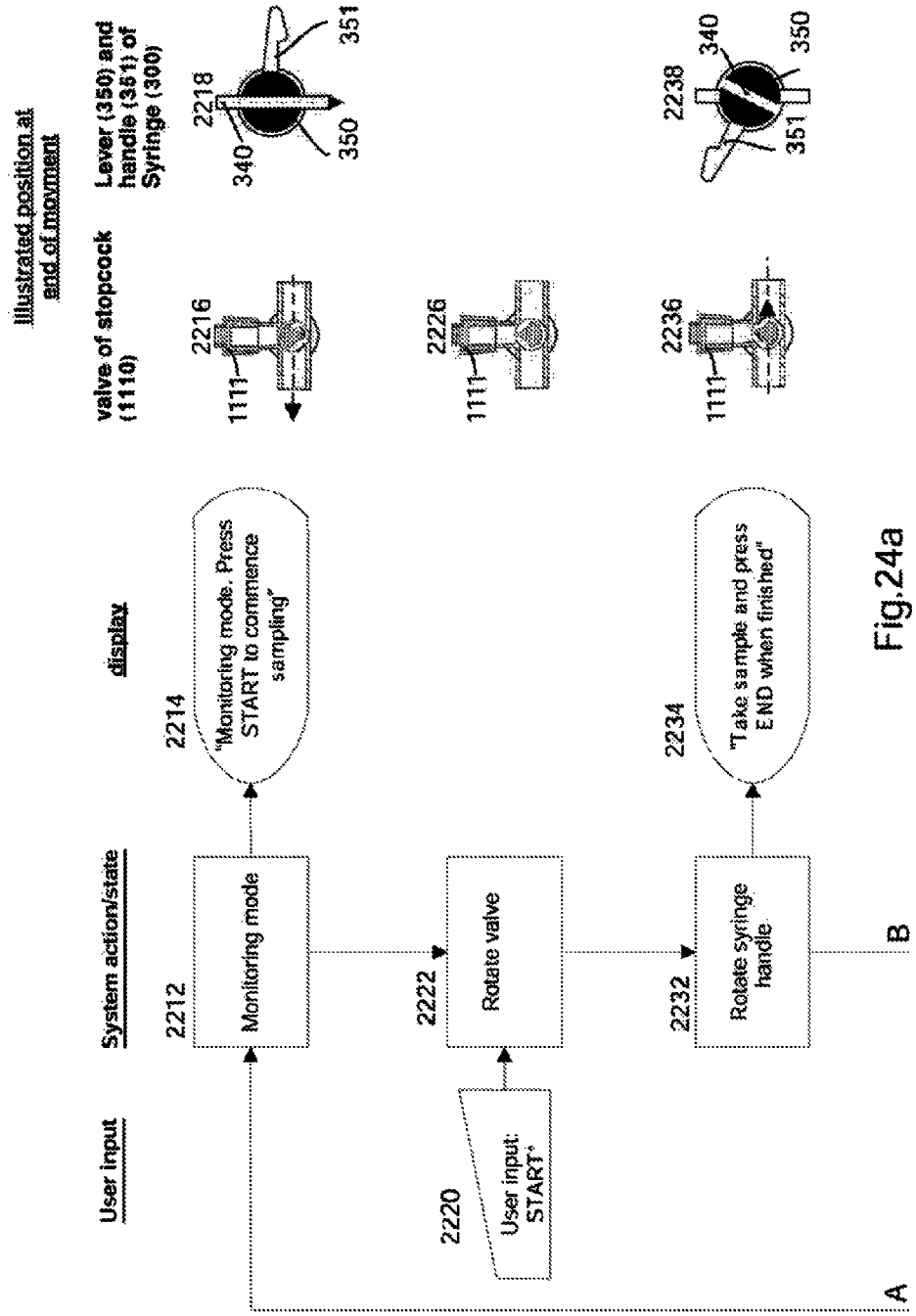

APPARATUS AND METHOD OF FLUID ASPIRATION

RELATED APPLICATIONS

This application is a continuation in part of PCT International Patent Application No. PCT/US2010/037043 filed Jun. 2, 2010, designating the United States of America and claiming priority from U.S. Provisional Patent Application No. 61/183,886 filed Jun. 3, 2009. This application also claims the benefit of U.S. Provisional Patent Application No. 61/414,427 filed Nov. 17, 2010, under 35 USC §119(e). The entire contents of each of the aforementioned applications are hereby incorporated by reference herein.

BACKGROUND OF THE INVENTION

1. Field of the Invention

The present invention relates to an In-Line sampling device and method for withdrawing (aspirating) blood from a patient fitted with a blood vessel catheter. More particularly, the present invention relates to a syringe enabled for aspirating blood into a sampling site in a closed manner, sealed from ambient air, in order to reduce the risk of human error and cross contaminations during the sampling process. Still more particularly, the present invention relates to a syringe, designed to operate manually or automatically and in synchronization with a sampling stopcock valve.

2. Prior Art

Sealed sterile blood sampling systems are known that have a dual function of introducing an upstream sterile fluid (e.g. saline solution) to a patient located downstream, and drawing back (aspirating) upstream fluid into the syringe. In a typical system, a small amount of infused fluid runs through the blood sampling line to the patient, when the line is not in use. This enables the blood sampling line to be maintained in a clear, unblocked/unclogged condition. When it is desired to take a blood sample from the patient, the fluid is aspirated beyond the sampling site so that a clean blood sample may be withdrawn. Relevant prior art documents that describe aspirating syringes or other syringe like aspirating devices said fluid sampling devices include the following.

U.S. Pat. No. 5,324,266 & U.S. Pat. No. 5,265,621 describe inline syringes which are operated linearly, namely the aspiration is performed by manually pulling the internal part of a syringe. This procedure may be physically strenuous due to the resistance of the gasket inside the syringe which may lead to accidental over aspiration. These patents further describe a sealing sleeve for maintaining a closed environment inside the syringe. This sleeve moves during aspiration, which can lead to ruptures or disengagement of the sleeve resulting in breach of the closed system. The linear operation of the syringe results in the extension of a piston beyond the syringe by a displacement equivalent to the aspirated volume, essentially doubling the length of the syringe. This is cumbersome in a hospital setting, and especially strenuous on a patient's arm. Additionally, operation of this "linear style" syringe requires the use of two hands, one to extract the piston, the other to prevent the syringe from moving.

U.S. Pat. No. 5,961,472 discloses a syringe which can be operated single handedly as opposed to the previous two patents discussed. However this syringe requires two independent squeezing motions instead of one, is not inline, and thus requires an additional valve system.

U.S. Pat. No. 5,374,401 discloses a blood sampling apparatus that uses a rotational movement to linear displacement of a piston via a threaded transmission system. This type of transmission involves high resistance due to friction of the thread. As a result high torque is exerted on a patient's arm (or stand) and could mask resistance of the fluid line due to occlusions. In addition this apparatus does not operate in-line and therefore requires an additional valve system, and is cumbersome to clean after aspiration. The exact amount of fluid aspirated is hard to determine as this apparatus does not incorporate a scale or any other measurement means.

U.S. Pat. No. 6,159,164 discloses a blood sampling system that does not operate in-line and therefore requires an additional valve system, and is cumbersome to flush and clean after aspiration. The exact amount of fluid aspirated is hard to determine as this apparatus does not incorporate a scale or any other measurement means. This system is operated by manually pushing an actuator towards the vertical axis of the apparatus which may result in torque that dislocates the apparatus from a patient's arm.

There are automatic systems for blood aspiration, for example, such as described in the U.S. Pat. No. 7,680,042 and US Published Patent Application No. US201010217154 and some of these systems incorporate use of integrated pressure monitoring. However, these systems cannot be operated manually, and most important, these systems do not operate in a closed manner, which allows the return of dead space fluids to patient, rather they discard these fluids as they are contaminated once aspired. In addition to the loss of fluids, working with systems that are not closed may result in higher contamination risks.

U.S. Pat. No. 5,758,643 is an example of a system that works in a closed manner and can return the dead space fluids to a patient; however, this system cannot operate manually and does not have an integrated pressure sensor for monitoring blood pressure.

None of the prior art described herein above enables the use of an automatic mode for aspirating syringes using an electronic system. Furthermore, pressure monitoring is required in many applications which require blood sampling; none of the prior art described above enable a device integrated pressure monitoring application.

SUMMARY OF INVENTION

The present invention provides an inline blood aspirating system that can operated both manually and automatically; works in a microbial closed manner; enables the return of aspirated fluids to a patient; incorporates an integrated pressure sensor to monitor the patient's blood pressure; results in simplicity of operation and reduction of expenses caused in duality of systems, one for aspiration and one for blood pressure sensing; operates simply and single handedly; does not require large forces to actuate and therefore, prevents aspiration overshoots and retains high sensitivity to tube occlusions.

When the system operates automatically, occlusion in the tubes may be detected electronically by measuring torque (current) on the drive shaft actuator during aspiration. Additionally, the system can include an actuated stopcock valve for automatic synchronization between syringe and the inlet/outlet to a patient.

Further, the present invention provides a syringe and system which is used to aspirate fluids from/to a patient. The syringe and system can be operated manually or automatically when connected to a novel electronic apparatus. The syringe is an integrated unit that is used for In-line fluid aspiration from a patient in a closed sterile manner. When a gasket (piston) retracts/returns in the syringe, the volume of air behind the gasket is allowed to escape/enter through a microbial filter or alternatively inflates/deflates a resilient membrane which acts as a balloon, these two optional methods result in a microbe free environment inside the syringe. The microbial filter can additionally have an anti-microbial agent such as silver ions to further sterilize the air passing through it. A given fluid volume can be precisely defined simply by single handedly rotating a valve to a predetermined volume according to a frontal volume scale. A locking position of the handle avoids rebound of the gasket as a result of the locked position of an undercut niche. A single handed valve/transmission rotating assembly enables a linear upward and downward displacement of the syringe gasket in a linear manner.

Having different geometry of the syringe housing and transmission ratio enables different design of the aspiration syringe according to predetermined performed procedures. The syringe can have a valve that shuts off an upper fluid inlet of the infused fluid whenever the valve is rotated in one sense (counter-clockwise) during aspiration. Alternatively, the syringe can have a valve which does not shut off the fluid channel in the closed position of the handle and in any rotated aspiration stage. The syringe can also incorporate a pressure transducer and has an additional vertically positioned port which enables (microbe filtered) air flow between an upper inlet and an open aired port for zeroing. The valve design enables closing a patient-side lower inlet and opening to air via a horizontally positioned port.

The aspirating syringe is designed to work manually using a front valve handle and automatically if plugged in to an electronic apparatus in a way that the back part of the valve engages to the electronic apparatus drive shaft. The syringe's pressure transducer is connected electrically to the electronic apparatus by means of cable or integrated connector.

The administrated fluids can be used to flush/clean the syringe and patient tubes by a flush mechanism which fully opens the line between the administrated fluid and syringe (normally it is only open to allow drip). This flush mechanism is designed to operate manually and activated by pulling a flush lever, or electromechanically operated when syringe is docked to the electronic apparatus. The manually operated flush device lever pull cord is designed to engage with a "U" type pulling electro-mechanical clamp when the syringe is docked to the electrical apparatus. When the syringe is plugged into the electrical apparatus, control of the aspiration procedure is automatic, mimicking the manual aspiration procedure.

When the syringe is operated automatically by the electronic apparatus, torque levels of the drive shaft are measured and the system indicates an occlusion which results in higher than normal torque which occurs because of resistance increase in the aspiration process.

A remote electromechanical stopcock system can be used when the syringe is operated automatically by the electronic apparatus. The system synchronizes the syringe positions and the stopcock movement in order to enable monitoring/aspiration/flushing and blood sampling. The electronic system is designed to operate any stopcock adapted to the motor housing and stopcock motor drive shaft.

The electronic system can incorporates a small air pump and pressure sensor connected to an infusion air pressure cuff in a way that the pressure cuff will increase the pressure in an IV-bag during the treatment time in order to maintain a positive pressure difference between the infusion flushing bag and patient blood pressure. The electronic system has a communication line port capable of transferring (by cable or wireless) pre-determined parameters and records to the bed side or to a computer network. The electronic system incorporates a built-in or separate display unit that is designed to display any pre-programmed information such as occlusion, pre-determined aspiration volume, time, patient name etc.

BRIEF DESCRIPTION OF THE DRAWINGS

FIG. 2a shows schematically a perspective view of a syringe;

FIG. 2b shows schematically an automatically operable syringe with an internal pressure transducer, mounted on an electronic control apparatus, connected to a patient;

FIG. 2c shows schematically a front view of the electronic control apparatus and remote control device, in an alternate position on top of electronic apparatus, with the syringe mounted thereon;

FIGS. 2d-g show schematically sample pressure waveforms indicating different pressure conditions as measured by a pressure transducer;

FIG. 3a-d show schematically a front view, a back view, a front cut section view, and a side cut section view respectively of a syringe;

FIG. 4a shows schematically an exploded perspective view of a syringe;

FIG. 4b-c show schematically a modification of the syringe with a different DPT connection;

FIGS. 5a and 5b show schematically a rack and pinion mechanism which drives the gasket inside the syringe;

FIGS. 6-9 show schematically different operating positions of the syringe with FIG. 6 showing the syringe in a zeroing position, FIG. 7 in an (open) monitoring position, FIG. 8 in a closed position with initial aspiration and FIG. 9 during further aspiration;

FIGS. 10a-g show schematically a zeroing and monitoring mechanism for a syringe;

FIG. 11 shows schematically a dual purpose latch mechanism for a syringe rotating lever;

FIG. 12 shows schematically a modified syringe without an integrated zeroing mechanism and having the fluid line embedded at the end of the fluid chamber.

FIG. 13 shows schematically a cross-sectional view of a modified syringe wherein the internal fluid line is telescopic;

FIG. 14 shows schematically a cross-sectional view of a modified syringe wherein the internal fluid line is flexible.

FIGS. 15a, 15b and 15c show schematically a sealing gasket, with the syringe in an initial position, pre-aspiration (FIG. 15a), following initial aspiration (FIG. 15b) and after maximum aspiration (FIG. 15c);

FIG. 15d shows schematically a perspective view of a sealing gasket;

FIGS. 16a-c show schematically a syringe with a flexible membrane that inflates during aspiration instead of venting air;

FIG. 17a shows schematically a sampling port strap for mounted on a bedside rail;

FIGS. 17b and 17c show schematically a sampling port device using a stopcock valve in an exploded front view (FIG. 17b), and in an exploded back view (FIG. 17c) showing the coupling mechanism;

FIG. 19a-c show schematically electronic and mechanical connections between a syringe and an electronic apparatus; FIGS. 19b and c, respectively, are assembled and disassembled cut views of the syringe and the electronic apparatus.

FIGS. 21a-f show schematically an example of some possible operational modes of the system of the present invention illustrating synchronizing of a syringe and sampling port mechanism.

FIGS. 22a-c show schematically a modification in which a MARVELOUS™ valve is used for the stopcock valve;

FIGS. 23a-c, 24a-b, 25a-b show schematically examples of different user/system action flow charts.

DETAILED DESCRIPTION OF THE INVENTION

Figure 1:
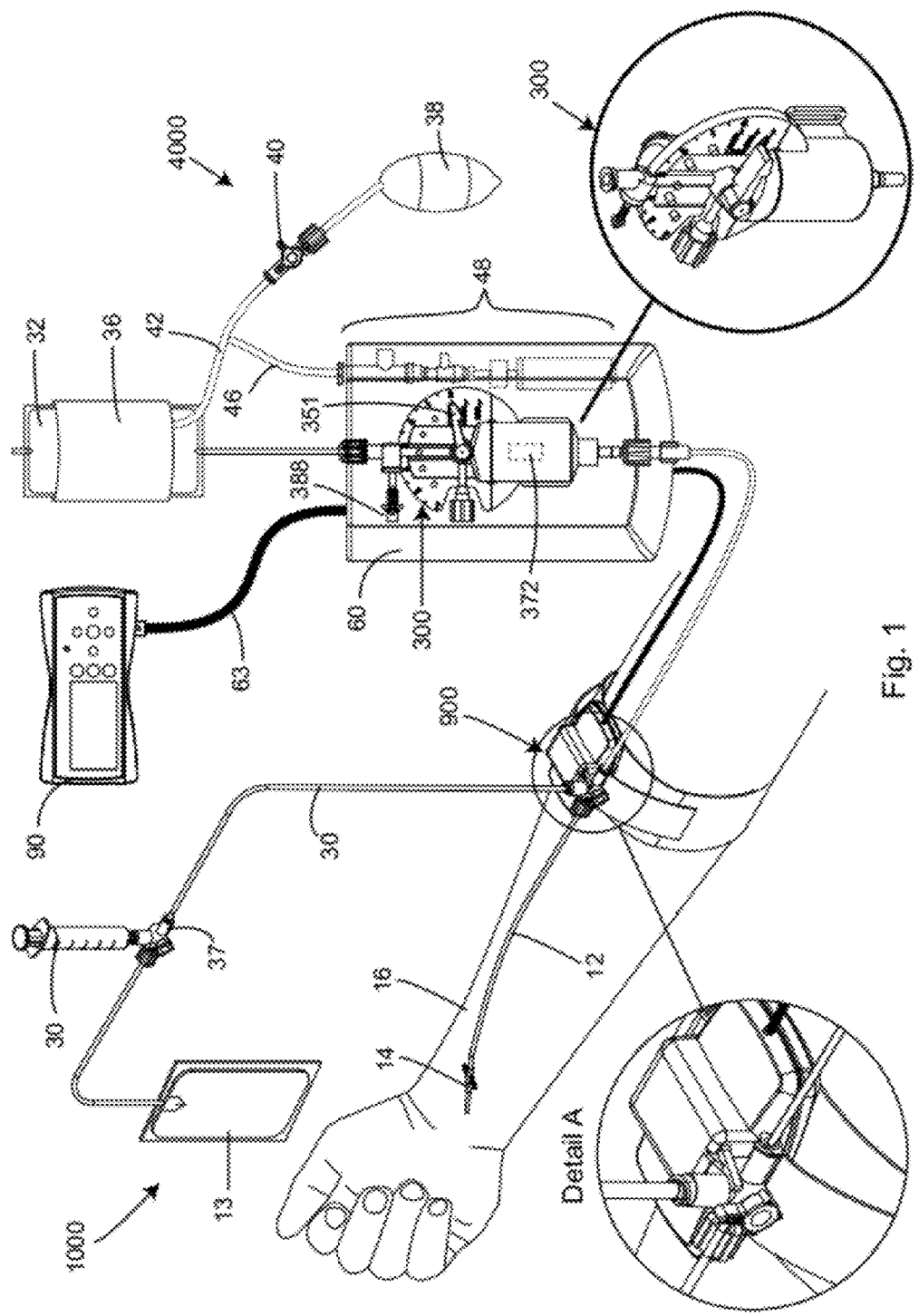
FIG. 1 shows schematically the assembled system of the present invention, wherein a syringe and sampling port device are coupled for in-line sampling and monitoring, and an auto pressurized cuff system retains infusion bag pressure.

A preferred embodiment of the blood sampling system of the present invention is shown in FIG. 1, referred generally as 1000, and consists of an automatic blood pressure measuring system with a sampling mechanism. System 1000 consisting of an IV bag (32) connected to a fluid line (12) leading from a catheter (14) embedded in a patient's arm (16). System (1000) comprises a sampling port mechanism (900) shown enlarged in Detail A, which is connected via side tube (35) to a stopcock valve (37) connected to a sampling collecting syringe (30) or any other sample collecting vessel (not shown) and through extension line (33) to a fluid waste collection bag (13) for in line analyzing of blood samples, which will be described in details hereinafter. A syringe (300) is mounted on an electronic apparatus (60). A cable (63) leads from the electronic apparatus (60) to a remote controller and display (90). The remote controller (90) controls the synchronization between sample port (900) and syringe (300). A pressure management system (4000), comprising a pressure cuff (36) that surrounding IV bag (32) is inflated or pressure released via a manual pump (38) through valve (40) via line (42). A branch line (46) leads to an automatic pump (48) which is a part of electronic apparatus (60), both of which will be described in detail hereinafter.

FIG. 2 shows an electronic apparatus (50) which is equivalent to electronic apparatus (60) except for the automatic pressure management system (4000) which is not present in the electronic apparatus (50). Additionally, the electronic apparatus (50) only automates the operation of the syringe (300) by remote control (910) and does not include a synchronization option with the sampling port mechanism (900).

As will be described hereinafter, the various specific embodiments of the present invention may be operable manually or automatically (via motor). FIG. 2a shows a manually operable syringe (300).

In FIG. 2b, automatically operable syringe (300) is mounted on an electronic apparatus (50) which is attached to the bedside of a patient (53). An IV bag (32) for introducing sterile fluid through syringe (300) is connected to electronic apparatus (50). Electronic apparatus (50) is positioned in a way that will enable a pressure transducer (not shown) inside syringe (300) to be on the same horizontal plane as the organ that is monitored for pressure measurements.

FIG. 2c shows remote control (910) in an alternate position on top of electronic apparatus (50). The front panel of remote control (910), comprises an on/off button (913) and a selected volume display (914) with control buttons for raising and lowering the settings. Control buttons for automatic aspiration (915), line opening (916), zeroing (917), performing an occlusion test (918), base line (919) and visual status lamp (57) are present on the panel.

A sterile fluid such as saline is typically introduced to a patient along a fluid conduit in order to prevent blockage of the conduit. However, blockage may nevertheless occur. If a change in the blood pressure reading occurs, it must be determined whether the change is due to an actual change in the physiological status of the patient, or due to a blockage or crimp in the fluid conduit joining the patient with the blood pressure reader, or any other glitch in one of the components of the system. The components of the present invention enable a practitioner to determine the source of a change in blood pressure reading, as described herein below.

Another means for indicating an occlusion, in addition to a change in the blood pressure reading, is a change in the resistance while withdrawing fluid into syringe (300), as will be mentioned hereinafter.

FIGS. 2d-g show pressure wave diagrams, as seen in monitor (80), indicating different pressure conditions as measured by a pressure transducer. The x-axis measures time and the y-axis measure pressure.

FIG. 2d shows a normal arterial line blood pressure waveform (334). The calibration of the pressure transducer to zero is indicated by the zeroed waveform (335).

FIG. 2e shows the normal arterial line blood pressure waveform (334).

When it is desired to verify a non-occluded status of the downstream conduit, fluid is aspirated into syringe (300) or any of the various syringes described herein below. A fast recovery (304) is shown in FIG. 2f along the waveform (334), indicating a non-occluded conduit. When a slow recovery (305) of the waveform (334) occurs, as shown in FIG. 2g, this is an indication of a partial occlusion of the fluid conduit.

FIG. 3a-d shows different views and cut sections of syringe (300). FIG. 3a is a front view of syringe (300) showing female inlet (390), flushing mechanism (380) situated upstream of proximal port and scale (362), rotating handle (351), side outlet (381), outlet cap (383), fluid chamber (310) and syringe outlet (311). Syringe (300) includes a housing (360) and a fluid chamber (310) within which is the gasket (322) that divides the internal space into a liquid side and an air side. Gasket (322) is driven by a rack and pinion mechanism by means of handle (351) connected at one end to rotary mounted shaft (350).

FIG. 3b is a back view of syringe (300), showing an antimicrobial filtered vent (365), coupler (302), which connects to shaft (65) of the above mentioned electronic boxes, integrated connector (374) of pressure transducer (not shown), and clips (371) for mounting the syringe on the electronic box.

FIG. 3c is a back section cut of syringe (300), showing shaft (lever) (350) with diametrical opening (340), fluid tube (330), fluid chamber (310) and gasket (322) surrounding the fluid tube (330).

FIG. 3d is a side section cut of syringe (300), showing its flushing mechanism (380), which consists of a flush lever (388), enclosed by a housing (391) and a cover (392), the coupler (302) connected to lever (350), and an internal pressure transducer (372) with its integrated connector (374).

In FIG. 4, syringe (300) of the present invention is shown in an exploded view in FIG. 4a, and in FIG. 4b-c, syringe (300) is modified with respect to the pressure transducer to form syringe (400) as shown. Syringe (400) connects the pressure transducer (472) by means of cable (473), instead of an integrated connector (374). The pressure transducers (372, 472) are integral components thereof—utilized in the blood pressure measuring system for continuously measuring a patient's blood pressure. All other elements in the syringe (400) and (300) are similar.

The syringe (300) seen in FIG. 4a has a flushing mechanism (380) situated upstream of proximal port and scale (362), and is connected with an upstream coupler (11) for connecting to upstream conduit (10). The flush lever (388), for selectively allowing and preventing fluid flow, is enclosed by a housing (391) and cover (392). Flushing mechanisms are standard features in the field, and have various designs that are well known in the art. An anti-microbial filtered vent (365) comprising a microbial filter, is preferably located in an opening (not shown) in housing (360) of syringe (300) for the purpose of admitting or discharging air from the air side of the gasket. The filtered vent (365) prevents bacteria and/or other undesirable microorganisms from entering into syringe housing (360) when air is expelled out of filtered vent (365) during the aspiration process, wherein gasket (322) is shifted within fluid chamber (310), as well as, when air is sucked into housing (360) through filtered vent (365) when the syringe returns to the line-open position. Filtered vent (365) or at least a portion thereof also is preferably treated with an anti-microbial agent, such as silver ions.

The blood pressure measuring system comprises a pressure transducer (372) located within fluid chamber (310), for measuring pressure along fluid tube (330) and a shaft (lever) (350) with handle (351) for selectively allowing and preventing fluid flow along fluid tube (330), as well as, for opening fluid tube (330) to atmospheric pressure for calibration of pressure transducer (372) via outlet (381), as described herein below. The lever (350) snaps to the coupler (302) which holds it in place at opening (301). Pressure transducer (372) is at least partially enclosed by casing (370), having an inlet (375). Inlet (375) is open to the atmosphere for allowing an internal membrane (not shown) within pressure transducer (372) to flex in order to sense and enable pressure to be measured along fluid tube (330). Casing (370) comprises a connector (374) having contacts that connect directly into a power supply (i.e. without a cable). Connector (374) extends out of the back (i.e. bottom) of syringe, although may be designed differently according to alternative specifications. Inlet (375) is positioned between the contacts of connector (374). Pressure transducer (372) can alternately be located along the syringe fluid line as part of the syringe body in locations (311) or along the fluid line at the proximal port (363) or outlet (311) indicated by arrows in FIG. 4a for the locations along syringe (300).

Volume regulator (320) comprises a gasket (322) for preventing leakage of fluid out of fluid chamber (310), and a drive portion (324) for shifting gasket (322) within fluid chamber (310). Gasket (322) is connected via coupling member (326) to drive portion (324). Gasket (322) comprises an internal radial groove (not shown) within which a radial disk of coupling member (326) is disposed. The geometrical shape of coupling member and the corresponding shape of gasket (322) is not limited to that shown herein, and may comprise any alternate design while performing essentially the same function as the components shown herein.

Drive portion (324) comprises a shifting mechanism for allowing drive portion (324) to shift gasket (322) within fluid chamber (310). The shifting mechanism is comprised of a rack (354) and pinion (356) for translating the rotational motion of the handle (351) via shaft (350) into linear motion of drive portion (324), as described herein below, but may alternatively comprise any suitable mechanism for enabling the shifting of gasket (322). The mechanical transmission mechanism is further explained with reference to FIG. 5. Clips (371) are fixed to the housing for mounting syringe (300) on a mounting board (not shown).

In FIG. 4b, an exploded view of internal pressure transducer (472) of syringe (400) is shown, where cable (473) and connector (474) extend from pressure transducer (472) for connecting to a power supply. Pressure transducer (472) is enclosed by casing (470), having an inlet (475). Inlet (475) is open to the atmosphere for allowing an internal membrane (not shown) within pressure transducer (472) to flex in order to enable pressure to be measured along fluid tube (430), as explained before. Detail B, shown in FIG. 4c, is an enlargement of the portion of syringe (400), illustrating a clamp (411) which secures cable (473) extending out of syringe (400) at the seam at which fluid chamber (410) and housing (460) are joined together. The outer tip of inlet (475) is shown extending out of clamp (411).

FIG. 5a shows a cut out and perspectives view of syringe (300) where the mechanical transmission mechanism of the syringe (300) is exposed. Pointer (352) is seen as protrusion of said handle (351). The function of pointer (352) being the indication in the scale (362) of the current operating status of the syringe (300), or any modifications of it thereof, and the aspirated fluid's volume level within the fluid chamber (310). Pointer (352) is an integral part and point in common to every modification to said syringe (300).

FIG. 5b shows an enlarged view of the mechanical transmission mechanism of the syringe (300). Upon rotation of the handle (351), clockwise or counter clockwise, the gasket (322) moves vertically down or up, respectively. The motion is achieved by a system of rack (354), located on drive portion (324), and pinion (356), co-axially mounted on the shaft (lever) 350 on handle (351), when the handle (351) and pinion (356) are rotated the rack (354) and drive portion (324) move vertically linearly in turn moving the gasket (322).

The interlocking toothed relationship between the rack and the pinion preferably enables a relatively fast linear displacement of the volume regulator. This allows a sensitivity to even a slightly higher resistance than usual during the displacement process.

FIGS. 6-9 show the main operational configurations of the syringe (300), showing the syringe in a zeroing position (FIG. 6), a monitoring position (FIG. 7) a closed position with initial aspiration (FIG. 8) and further aspiration (FIG. 9).

A top view of syringe (300) is shown in a partial cross-section in FIGS. 6C, 7C, 8C and 9C, showing fluid chamber (310) partially cut along fluid tube (330), as well as a cross-section of outlet (381). Syringe (300) is in the zeroing position in FIG. 6C, in the monitoring position in FIG. 7C, in the initial aspiration position in FIG. 8C, and in a further aspiration position in FIG. 9C.

Prior to operating the blood pressure measuring system, pressure transducer (372) must be calibrated (zeroed) to ensure accurate readings. With reference to FIGS. 6A, B and C, in order to zero the pressure transducer (372), shaft (lever) (350) is turned to the "zero" indicia, in which the longitudinal axis of diametrical opening (340) is rotated such that fluid is prevented from flowing through fluid tube (330), shown in FIG. 6C, while simultaneously allowing communication between pressure transducer (372) and the atmosphere via outlet (381). Particularly with reference to FIG. 6A, shaft (lever) (350) comprises a flow conduit (353) for enabling air flow between fluid tube (330) and outlet (381).

Apertures (332) (see enlarged Detail 6B) located near the closed tip (333) of fluid tube (330), through which fluid flows, are covered by ring element (328) of gasket (322) when zeroing pressure transducer (372), thereby blocking air-flow communication with a patient. As mentioned, tip (333) of fluid tube (330) is closed. In an alternative version (not shown), fluid tube (330) is a solid line (i.e. without apertures (332)), and open at its tip, wherein a cap, comprising apertures around its periphery is fixedly positioned on the tip.

FIGS. 7A, B and C, show the monitoring mode in which the handle (351) is turned to the "open" indicia, causing the longitudinal axis of diametrical opening (340) to be rotated such that fluid tube (330) is open to the upstream conduit (10) via opening (340). In the monitoring mode, the pressure transducer (372) is closed to the atmosphere and is open to the fluid tube (330) which leads to the patient and allows blood pressure monitoring. Additionally, in the monitoring mode the gasket (322) is moved (retracted) along fluid tube (330) to expose the orifices in tip (333) which enables the connection of fluid tube (330) to the patient as mentioned above. The movement of gasket (322) is shown in 7B.

FIGS. 8A, B and C, show the closed position with initial aspiration mode, in which handle (351) is turned to the "close" indicia, and the longitudinal axis of opening (340) is rotated such that fluid tube (330) is cut off from the upstream conduit (10) effectively disconnecting the patient from the upstream conduit (10). FIG. 8B further illustrates gasket (322) position in this configuration.

FIGS. 9A, B and C, show the aspiration mode in which the handle (351) is turned to any position on the scale above the "close" indicia. The longitudinal axis of opening (340) is rotated such that fluid tube (330) is closed to the upstream conduit (10). FIG. 9B further illustrates the position of gasket (322) in this configuration.

It should be noted that although not mentioned explicitly, syringe embodiments which perform zeroing of a pressure transducer by exposure to atmospheric pressure, can do so through a microbial filter or other mechanism to prevent bacteria and/or other undesirable microorganisms from entering into the syringe housing.

FIG. 10a-g shows an alternative syringe (500) with a modified shaft (lever) (350) design. FIG. 10c shows syringe (500) in the monitoring position while the shaft-handle (550) is in position noted by numeral '0' and FIGS. 10a, b are the corresponding front and back views of the pinion (556) and rack (554), respectively.

FIG. 10f shows the syringe (500) in the zeroing position while the shaft-handle (550) is in position noted by letter 'Z' and FIGS. 10 d, e are the corresponding front and back views of the pinion (556) and rack (554), respectively. And FIG. 10g is the corresponding cut section which illustrates the connective channels (513), (511) and grooves (551), (552) in the shaft-handle 550.

When shaft-handle (550) is in any of the aspirating/monitoring positions, namely, any position which is counter clockwise relative to (including) the position noted by numeral '0' then the fluid channels (511) and (512) are connected by the circumferential groove (551) which is located on the axis of the shaft-handle (550) see DETAIL C. The pinion (556) and rack (554) are engaged in all the working positions and translate the rotational displacement of shaft-handle (550) to the linear displacement of the gasket (522) for aspiration as shown above in syringes (300, 400). The pinion (556) disengages the rack (554) at the shaft-handle position noted by numeral '0' as shown in FIG. 10c wherein any additional rotation of the shaft-handle (550) clockwise does not translate into linear motion of the gasket (522) this is achieved by a pinion (556) that has teeth on only part of its circumference, and a rack (554) which has the last tooth (523) chamfered as shown in the front view FIG. 10a and detail C. When the lever (550) is further rotated clockwise beyond the position noted by numeral '0', the teeth of pinion (556) are completely disengaged from the teeth of the rack (554) FIG. 10d-e, in order to re-engage contact between the pinion (556) and rack (554) for counter clockwise rotation of the shaft-handle (550) beyond the position noted by numeral '0', a pin (557) located on the pinion (556) latches into a groove located on the rack (554) FIG. 10e. While the shaft-handle (550) is rotated clockwise beyond the position noted by numeral '0', the fluid channels (511) and (512) disengage and the fluid channel (511) is connected to the air channel (513) by the by-pass groove (552) located circumferentially on the axis of the shaft-handle (550) as shown in Detail d, this allows the zeroing of pressure sensor (572) which is connected along the path of fluid channel (511) and integrated at top of syringe (500) under flushing mechanism (580) (FIG. 10c) by exposure to atmospheric pressure.

Syringe (500) can be docked to a suitable electronic apparatus similar to the electronic apparatus (50, 60) with slight adjustments to the electro and mechanical connectors suitable to syringe (500), such as a different location for the pressure sensor socket.

FIGS. 11(A-D), show a latching mechanism (570) of syringe (500) used as a stopper and as a latch for the handle (553) of shaft-handle (550). The shaft-handle (550) is rotated along the range of the syringe (500) within the range noted by numeral '0' and '7'. When the handle (553) and shaft-handle (550) rotate clockwise to the position designated by numeral '0' on the scale, (A) the handle (553) sets into a groove (501) which creates a mechanical hold on the handle and shaft-handle and prevents accidental aspiration by non-intentional rotation of the shaft-handle (550) counter clock wise. Under regular working conditions, namely when zeroing of a pressure sensor is not required, the shaft-handle (550) is physically constrained clockwise by the latching mechanism (570) which acts as a mechanical stopper under these conditions (A, B). When zeroing is required, the shaft-handle (550) is rotated clockwise until stopped by the latching mechanism (570) shown in B, the latching mechanism (570) is then manually pulled away (C) to allow shaft-handle (550) to further rotated clockwise beyond the latching mechanism (570) and the latching mechanism (570) is then returned to its initial state (D). The latching mechanism (570) is held in place by means of elastic tension (C) by an elastic connector (571).

FIG. 12 shows a further modified syringe (600). This syringe (600) does not have an integrated zeroing mechanism as syringe (500, 400, and 300) herein shown above, rather it achieves zeroing of the pressure transducer (672) by opening an additional valve (614) as explain below.

When the handle and shaft-handle (650) rotates clockwise to the position designated by numeral '0' (Detail E) the handle sets into the groove (601) which creates a mechanical hold on the handle and shaft-handle and prevents accidental aspiration by non intentional rotation of the shaft-handle (650) counterclockwise as shown in FIG. 11 of syringe (500). In FIGS. 12b-12d, shaft-handle (650) has a circumferential groove (651) which allows the passage of fluids from fluid tube (610) to fluid tube (611) regardless of the shaft-handle (650) orientation. A pressure transducer (672) is situated in syringe (600) as shown below flush mechanism (680).

Zeroing is achieved by rotating valve (614) in a manner which disconnects the patient and fluid tube (613) and connects the fluid line (611) to the orifice (612) which is exposed to atmospheric pressure.

Details F, G and FIG. 12e show the end of the fluid line (611) extending beyond the extreme position of the gasket (622) and embedded within the body of the fluid chamber (621). This provides additional axial rigidity to the fluid line (611) which could otherwise be bent out of the axial position by forces resulting in vertical displacement of the gasket (622). FIG. 12e shows a cut out section of the end of the fluid line (611) embedded in the body of fluid chamber (621) and further shows the fluid channels (623) which allow passage of fluid to and from the fluid chamber and the extended fluid tube (613) leading to patient. In the monitoring state, flow is achieved through the fluid line (611) to fluid tube (613), and during aspiration, fluid is extracted from fluid tube (613) (patient) to the fluid chamber (625) via the four fluid channels (623).

The syringe (600) can alternatively be without the pressure transducer (672) and accordingly without the entire valve (614) as no zeroing is required. Regardless of whether or not the pressure transducer (672) is used, a flush mechanism (680) is always obligatory for this syringe (600) as the shaft-lever (650) is constantly open across the fluid line as explained above.

The following descriptions of syringe embodiments include syringes that do not have any pressure transducer and are only used in blood pressure monitoring lines for aspiration during blood sampling.

FIG. 13 shows the cross section of syringe (100). The fluid line is telescopically composed of two sections (132) and (134), wherein fluid chamber (110) is shown at the maximum volume capacity (or, the final position), as seen enlarged in 13A, wherein line section (132) telescopically overlaps first line section (134). In 13B the fluid chamber (110) is shown at the minimum volume capacity (or, the initial position) and section (132) is telescopically extended and only minimally overlaps with first line section (134).

FIG. 14 shows syringe (150) in a cross section. Syringe (150) is similar to syringe (100) and differs by having a flexible fluid tube (130) instead of a telescopic fluid line.

FIGS. 15a-c introduces and describe syringe (200). A partial cutout of a first side of fluid chamber (210) of the assembled syringe (200) is taken along a portion of fluid chamber (210), distally towards opening (212), and shows in FIG. 15a syringe (200) in its initial position, in which fluid flows through fluid tube (230) and no aspiration is performed; in FIG. 15b, in which an initial aspiration is performed; and in FIG. 15c, in the final position in which maximum aspiration is performed. Gasket (223) is shown in a perspective view in FIG. 15d and has a protruding ring element (228) located at the opening of gasket (223), which is positioned around the end of fluid tube (230), as seen enlarged in Detail H in FIG. 15a. Protruding ring element (228) enables a laminar blood flow, which thereby reduces the potential of hemolysis from occurring as the blood flows from fluid tube (230). Ring element (228) is preferably an integral terminal portion of gasket (223). The gasket (223) shown in syringe (200) is suitable and can be used in all other relevant syringe embodiments.

In a further modification, instead of an anti microbial vent, which is relevant to all the described syringes, all syringes may comprise an elastic membrane seal which inflates with the movement of the gasket and the drive portion during aspiration and deflates during reverse motion of the gasket and drive portion, for maintaining a totally closed environment, sealed from the ambient air and for preventing any contamination that might otherwise occur with the presence of a vent. FIGS. 16a-c show an example of the inflation of the mentioned elastic membrane seal (271) during aspiration for the syringe (200) at the initial, median and final position of the gasket (222) in FIGS. 16a, b and c, respectively.

Herein below the embodiments of blood sampling system (1000) of FIG. 1 are explained in detail.

In FIG. 17a sampling port mechanism (900) is mounted on a bedside rail (52) via strap (51), or alternatively may be mounted on any similar profile. Any suitable mounting means may be utilized. The strap (51), as shown in the figures herein, is preferably re-sealable and open-able via Velcro™, buckle, latch, etc. Syringe (300) works in synchronization as will be explained in further details with reference to FIGS. 21-26 with the sampling port mechanism (900) to enable monitoring, sampling, flushing and dead space retrievals in a closed sterile manner.

FIGS. 17b-c show exploded front and back views respectively, of sampling port mechanism (900). Referring to FIGS. 17b and c, sampling port mechanism (900) comprises a lower casing (1201) for housing an inner frame (1202), which surrounds an electric board (PCB) (1203) preferably having a wireless transmitter/receiver (1210) or wire (not shown) connection, a power source (battery) (1207) for providing power to the electronic circuitry and to a motor (1204) having a shaft (1211) for coupling with stopcock valve (1100) via coupler (1206). Coupler enters valve through opening (1212) as seen in FIG. 17b. Alternative valves may be used, requiring unique coupling mechanism and corresponding openings. Motor (1204) is secured in place with a clamp (1208). Sensor system (1205) enables feedback regarding the position of stopcock. Upper casing (1209) encloses the components surrounded by inner frame (1202).

Figure 18:
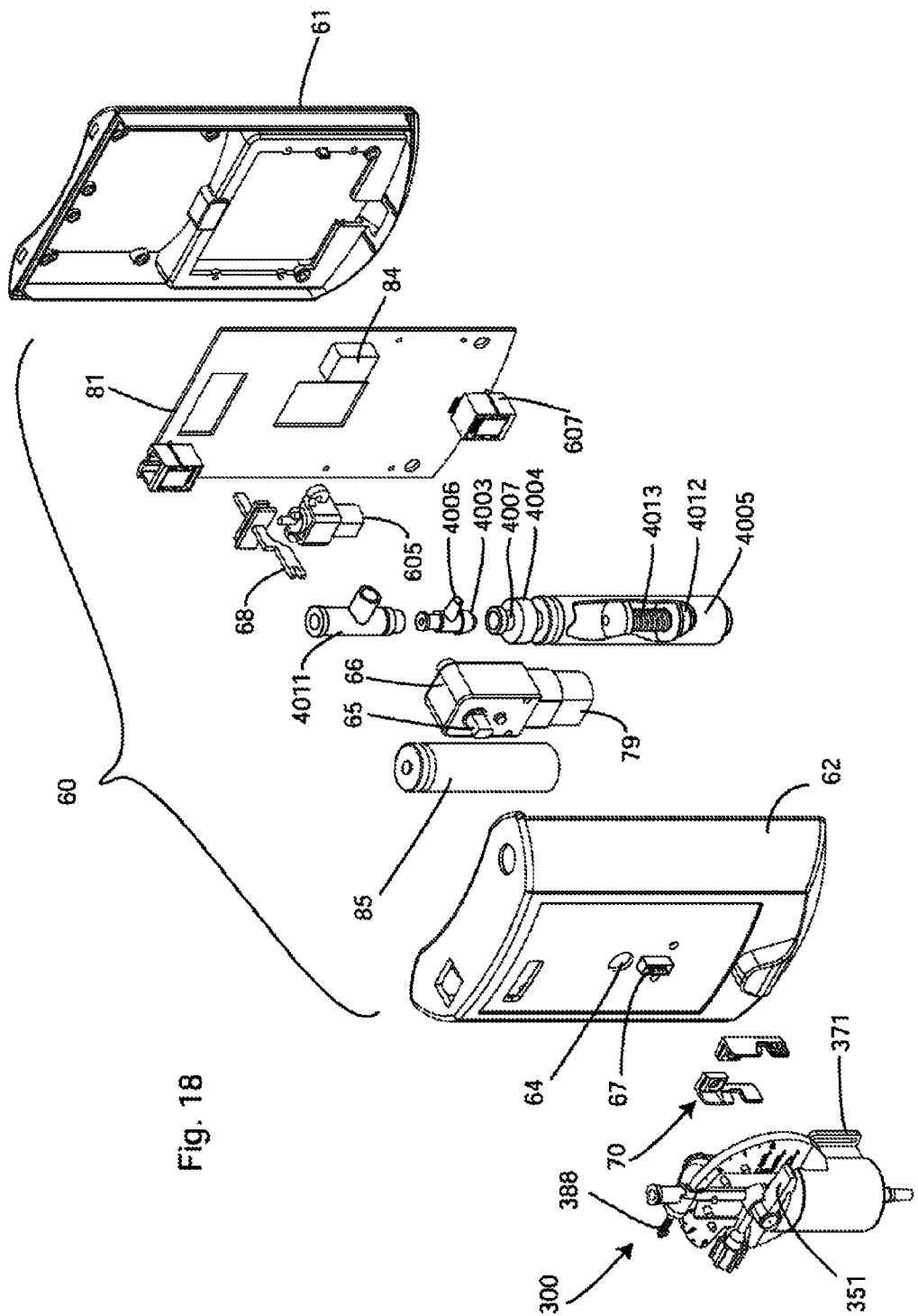
FIG. 18 shows schematically an exploded view of an electronic control system.

Syringe (300) and an exploded view of the electronic apparatus (60) are shown in FIG. 18. The electronic apparatus (60) mounts syringe (300) via clips (70) that protrude from the front panel (62). An electric circuit board (PCB) (81), syringe actuator (79), flushing plunger holder (68), flushing plunger actuator (605), and battery (85) are mounted between front panel (62) and back panel (61). The battery (85) supplies power to the electronic apparatus (60). Syringe actuator (79) comprises a gearbox (66) and a shaft (65) for extending through opening (64) in front panel (62), and coupling with syringe (300) for rotating handle (351). Flushing plunger actuator (605) operates the flush lever (388) of syringe (300). The electric circuit on board (81) receives and transmits data from port (607) via cable (not shown), or from wireless transmitter (84). Also situated between front panel (62) and back panel (61) are some of the components of the automatic pressure management system (4000).

Pressure is retained in infusion bag (12) shown in FIG. 1, by automatic pressure management system (4000). Pressure can build up in cuff (4001) initially by manual pumping of manual pump (4002) or automatically by electric pump (4005). Pressure in cuff (36) can be released at any time by manually rotating valve (40) also shown in FIG. 1, or via electromechanical valve (4011). Flow backlash into tube (4007) is prevented by check valve (4003).

The second possible pressure management system utilizes pressure transducer (4004), which measures the pressure in the line leading to cuff (36). When the system measures a drop below a preselected or designated threshold, the electric pump (4005) retracts (is energized) and sucks air via orifice (4006) down tube (4007) wherein suction through tube (46) is prevented by check valve (4003). Following the retraction, electric pump (4005) compresses air into cuff (36) through tubes (4007) and (46), wherein release through orifice (4006) is prevented by check valve (4003). Retraction and compression steps are repeated until the desired pressure is obtained in cuff (36).

Control and monitoring of the pressure in cuff (36) and actuation of electric pump (4005) are performed by a microprocessor unit in electronic apparatus (60). Electric pump (4005) comprises a piston (4012) with an electrical drive mechanism (4013). In the event of over-pressurization in the system, the pressure can be released via electromechanical valve 4011. Alternatively, any other type of suitable pump may be used.

FIG. 19a-c shows the electronic and mechanical connections between the syringe (300) and the electronic apparatus (60). FIG. 19a shows the syringe (300) coupled to the electronic control apparatus (60). FIGS. 19b and c show an assembled and disassembled cut version of apparatus (60) respectively. In FIG. 19a, syringe (300) is seen docked to electronic apparatus (60) via clips (70) that snap into the grooves of fittings (371). The shaft-lever (350) of syringe (300) is engaged in opening (301) (FIGS. 19b and c) via coupler (302) by syringe actuator (79), through shaft (65), shown assembled in FIG. 19b. The flush lever (388) is shown engaged by actuator (605) (FIG. 19b) via flushing plunger holder (68). The pressure transducer (372) sends data to electric circuit board (81) through the joint connectors (374) of syringe (300) and (67) of electronic apparatus (60).

Figure 20:
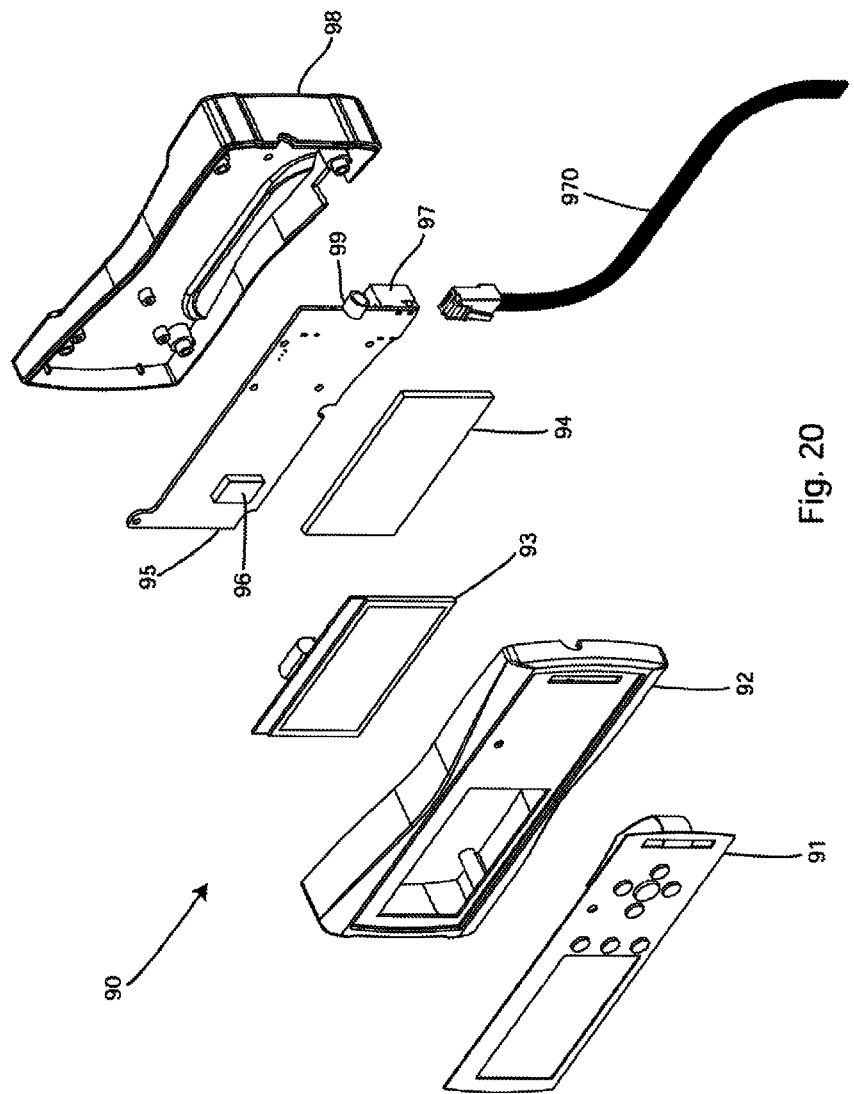
FIG. 20 shows schematically an exploded view of a remote controller.

Referring to FIG. 20, an exploded view of the remote control (90) is shown comprising a control panel (91) with an array of control buttons, a front cover (92), a display (93), a battery (94) for providing a power source, an electric circuit board (95), a back cover (98), a serial port (97), a wireless transmitter/receiver (96) and DC port (99). Remote control (90) receives and transmits data by serial port (97) via cable (970) or wireless transmitter/receiver (96). DC port (99) can be used to power remote control (90) and/or charge battery (94). Alternatively, remote control (90) may be used to control sampling port mechanism (900) exclusively. Remote control (90) enables user to input commands and data to electronic apparatus (60) and displays information including but not limited to alarms, system status and system information.

FIGS. 21a-f show an example of two of many possible operational modes of the system (1000) of the present invention which show the synchronized operation of the syringe (300) mounted on electronic apparatus (60), sampling port mechanism (900) and remote control (90). The specific steps and/or the sequence of the steps shown herein may differ depending on various considerations such as hospital protocol. This embodiment shows two sequential stages in the process of monitoring and sampling, using a stopcock valve (1100).

FIG. 21a shows the initial (or monitoring) state of the system (1000). Stopcock valve (1100) of sampling port mechanism (900) and shaft-lever (350) of syringe (300) are oriented such that sterile fluid (e.g. saline) runs from an infusion bag along infusion tube to the patient. A schematic cross-sectional view of the lever (350) of syringe (300) is shown in FIG. 21c, showing sterile fluid, indicated by dotted arrow (950), flowing through shaft-lever (350). FIG. 21a shows a schematic cross-sectional view of stopcock valve (1100), showing sterile fluid, indicated by dotted arrow (951), flowing through stopcock valve (1100) and closed to the sampling port (1900).

FIG. 21e shows step one of the fluid sampling process, in which system (1000) is in the aspiration state. Handle (351) is rotated to close shaft-lever (350), thereby preventing fluid flow through syringe (300) from infusion tube to patient, as shown in FIG. 21f. The rotation of handle (351) pulls gasket (322) through the fluid chamber (310) of syringe (300), causing aspiration of saline and blood through the stopcock valve (1100), while closed to the sampling port (1900), as shown in FIGS. 21d and e.

FIGS. 22a-c show an alternative aspect of the present invention, in which the stopcock valve (1110) of the sampling port mechanism (900) comprises a MARVELOUS™ valve according to U.S. Pat. No. 7,984,730B2. FIG. 22a shows system (900) in the monitoring state. FIG. 22b shows a top view of sampling port mechanism (900), and FIG. 22c shows a cross-sectional view of the MARVELOUS™ stopcock valve (1110) cut along line A-A of FIG. 22b. In FIG. 22c the MARVELOUS™ stopcock valve (1110) is shown allowing saline to flow through MARVELOUS™ stopcock valve (1110), avoiding the elastic membrane of a luer activated sampling port (1111).

Figure 23B:
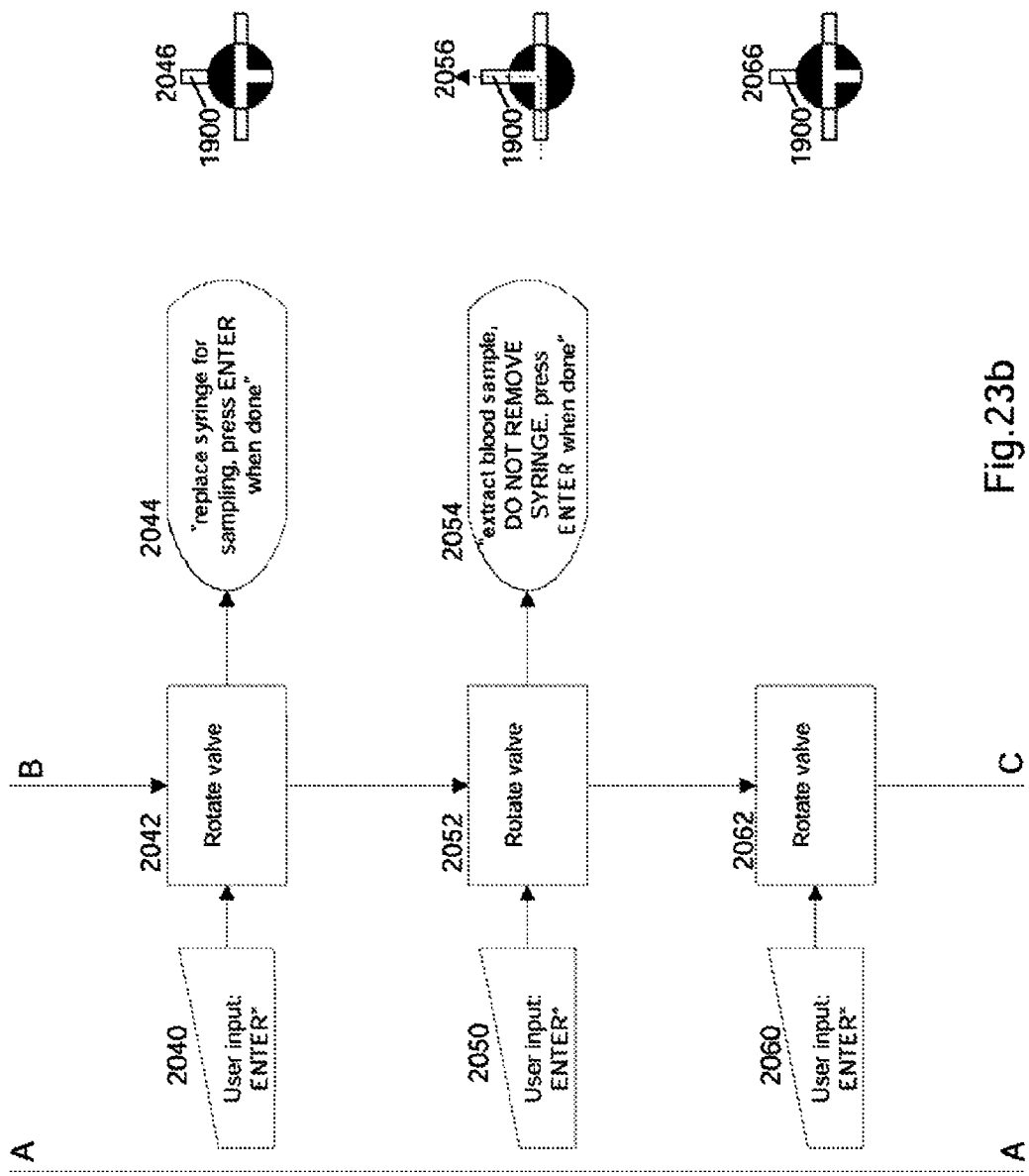

FIGS. 23a-c show a flow chart of the sequential steps of synchronization between the four way stopcock at the sampling port mechanism (900), and syringe (300) controlled by electronic apparatus (60) and a remote control (90). These Figures show the user input, system action/state, display, shown on the remote control after the completion of the action/state, the schematic positions of the stopcock valve (1100) and the position of the shaft-lever (350) and handle (351) of syringe (300).

In FIG. 23a the system is shown in monitoring mode, action (2012), where stopcock position (2016) shows stopcock (1100) open from the IV bag to the patient and closed to the sampling port (1900) and in position (2018) of syringe (300) the opening (340) of the shaft-lever (350) is positioned such that flow is open from the IV bag through stopcock valve (1100) to the patient and the display mode (2014) will indicate "Monitoring mode. Press START to commence sampling."

Once the user press START, input (2020), the system rotates the syringe handle (351), action (2022), causing the handle (351) of shaft-lever (350) of syringe (300) to rotate counterclockwise, action (2028), thus aspirating blood from the patient and closing the flow of saline from the IV bag to the patient, while stopcock (1100) remains in position (2016), allowing the passage of blood, and the display mode (2024) will indicate "Connect wash syringe, press ENTER when done". At this stage, the caregiver will connect a wash syringe, which can be any type of empty syringe, to the sampling port (1900).

Once the user press ENTER, input (2030), the system rotates the valve, action (2032) of the stopcock (1100), thus opening the stopcock to the sampling port (1900), where the washer syringe was connected, in order to withdraw the saline left inside the sampling port (1900) thus allowing the subsequent withdrawal of a clean blood sample, and the display mode (2034) will indicate "extract fluid, DO NOT REMOVE SYRINGE, press ENTER when done".

In FIG. 23b, once the user press ENTER, input (2040), the system rotates the valve, action (2042), of the stopcock (1100), thus closing the stopcock to the sampling port (1900), thus allowing the removal of said washer syringe, and the display mode (2044) will indicate "replace syringe for sampling, press ENTER when done". Since the stopcock is closed to the sampling port (1900), the caretaker, at this stage, can safely replace the washer syringe with the blood sampling syringe.

Once the user press ENTER, input (2050), the system rotates the valve, action (2052), of the stopcock (1100), thus opening the stopcock to the sampling port (1900), allowing the blood sampling syringe to withdraw clean blood sample, and the display mode (2054) will indicate "extract blood sample, DO NOT REMOVE SYRINGE, press ENTER when done". The caretaker at this stage will withdraw clean blood sample.

Once the user press ENTER, input (2060), the system rotates the valve, action (2062), of the stopcock (1100), thus closing the stopcock to the sampling port (1900), while the blood sampling syringe is still connected.

As shown in FIG. 23c, the system will then rotate the syringe handle, action (2072), causing the handle (351) of shaft-lever (350) of syringe (300) to rotate clockwise, action (2078), thus allowing the saline/dead-space and blood left in the system to return to the patient, and the display mode (2074) will indicate "you can now remove sample syringe and replace with flush syringe, press ENTER when done"

Once the user press ENTER, input (2080), the system rotates the valve, action (2082), of the stopcock (1100), thus closing the patient line to allow flushing of the sampling port (1900). The system will then actuate the flusher, action (2092), thus allowing saline to flush blood out of the sampling port and into the flush syringe. The system will then rotated the valve, action (2102), thus closing the stopcock to the sampling port (1900), allowing the system to return to the monitoring stage, and having the display mode (2104) indicate "you can now remove flush syringe". The caretaker, at this stage, can safely remove the flush syringe.

Figure 24B:
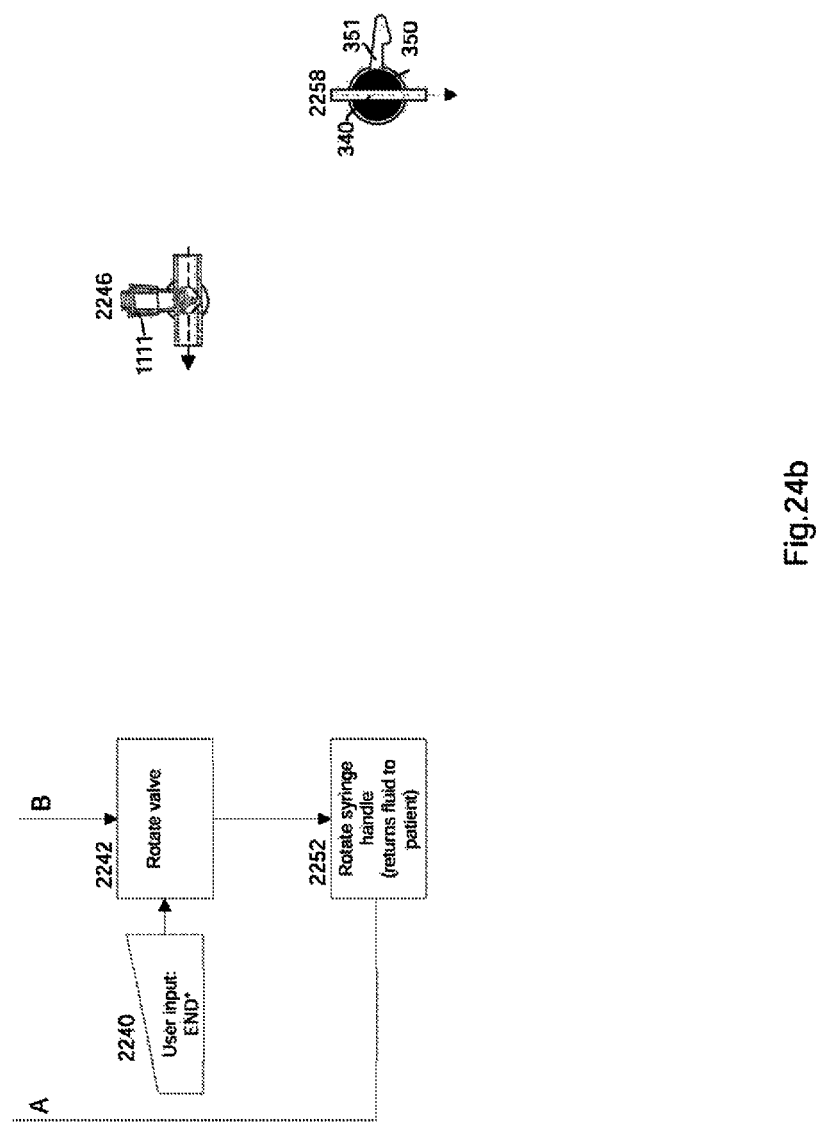

FIGS. 24a-b show an example of the user/system action flow charts for the MARVELOUS™ stopcock valve (1110). In FIG. 24a, the system is shown in monitoring mode, action (2212), stopcock position (2216) shows stopcock (1110) open from the IV bag to the patient and closed to the luer activated sampling port (1111), and in position (2218) of syringe (300) the opening (340) of the shaft-lever (350) is positioned such that flow is open from the IV bag through stopcock valve (1110) to the patient and the display mode (2214) will indicate "Monitoring mode. Press START to commence sampling".

Once the user press ENTER, input (2220), the system rotates the valve, action (2222) of the stopcock (1110), thus opening the stopcock to the luer activated sampling port (1111), thus allowing the subsequent withdrawal of a clean blood sample.

The system then rotates the syringe handle, action (2232), causing the handle (351) of shaft-lever (350) of syringe (300) to rotate counterclockwise, action (2238), thus aspirating blood from the patient and closing the flow of saline from the IV bag to the patient, while stopcock (1110) remains in position (2226), allowing the passage of blood, and the display mode (2234) will indicate "Take sample and press END when finished". At this stage, the caregiver will connect a sample syringe, which can be any type of empty syringe, to the sample luer activated port (1111).

In FIG. 24b, once the user press END, input (2240), the system rotates the valve, action (2242), of the stopcock (1110), thus closing the stopcock to the luer activated sampling port (1111), allowing flow of saline to the patient.

The system will then rotate the syringe handle, action (2252), causing the handle (351) of shaft-lever (350) of syringe (300) to rotate clockwise, action (2258), thus allowing the saline/dead-space and blood left in the system to return to the patient.

Figure 25A:
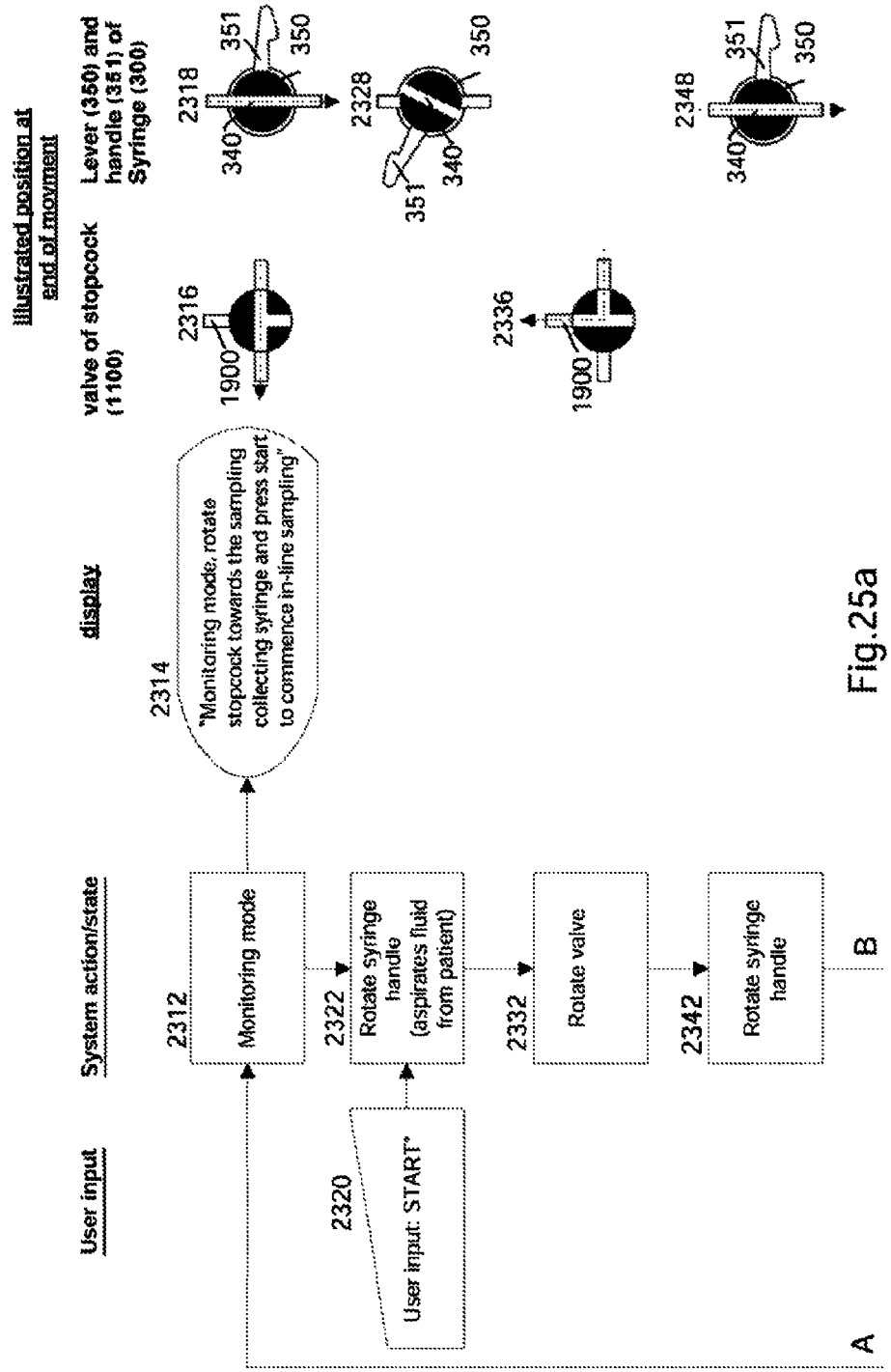
Figure 25B:
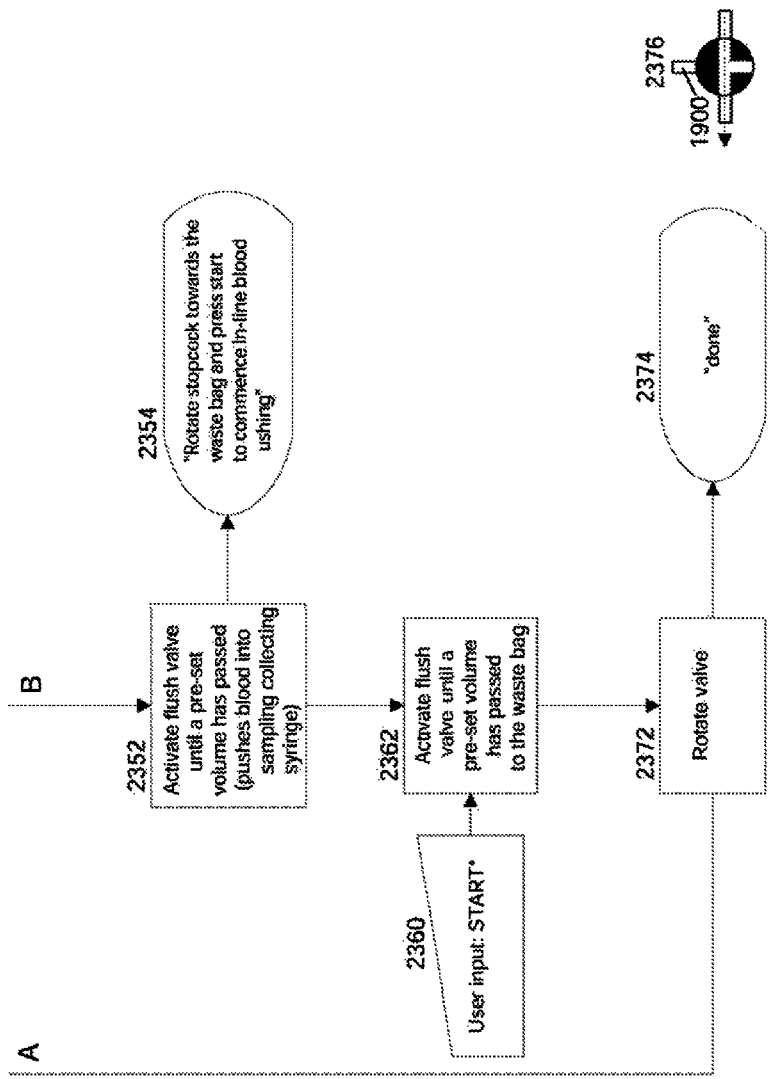

FIGS. 25a-b show an example of the user/system action flow charts, using a sampling collecting syringe (30) and waste bag (13) for in-line sampling. Throughout the various operational steps, system positioning (syringe (300) and valve (1100)) and pressure is monitored and will set off an alarm if system malfunctions or reaches any dangerous scenarios as pre-defined in the software.

In FIG. 25a, while in monitoring mode (2312), stopcock position (2316) shows stopcock (1100) open from the IV bag to the patient and close to the sampling port (1900) and in position (2318) of syringe (300) the opening (340) of the shaft-lever (350) is positioned such that flow is open from the IV bag through stopcock valve (1100) to the patient and the display mode (2314) will indicate "Monitoring mode. Rotate stopcock towards the sampling collecting syringe and press START to commence in-line sampling".

Once the user press START, input (2320), the system rotates the syringe handle, action (2322), causing the handle (351) of shaft-lever (350) of syringe (300) to rotate counterclockwise, action (2328), thus aspirating blood from the patient and closing the flow of saline from the IV bag to the patient, while stopcock (1100) remains in position (2316), allowing the passage of blood.

In action (2332), the system rotates the valve of the stopcock (1100) to position (2316), thus opening the stopcock to the sampling port (1900) and from there to the sampling collecting syringe (30) of FIG. 1, not shown.

In action (2342), the system rotates the syringe handle clockwise, position (2348), of syringe (300), thus allowing the introduction of the withdrawn blood into an auto-analyzer through stopcock valve (1100). At the end of the rotation, the opening (340) of the lever (350) is positioned such that flow is open from the IV bag through stopcock valve (1100) to the sampling collecting syringe (30), not shown, while stopcock (1100) remains in position (2336).

In FIG. 25b, action (2352) is shown, where the system activates the flush valve until a pre-set volume of blood has passed into the sampling collecting syringe (30), not shown, while stopcock (1100) remains in the previous position (2336) and the syringe (300) remains in position (2348) and the display mode (2354) will indicate "Rotate stopcock towards the waste bag and press START to commence in-line blood flushing".

Once the user press start, input (2360), the system activates the flush valve, action (2362), until a pre-set volume has passed, washing the tested blood out of the line all the way through into the waste bag (13) of FIG. 1, not shown.

In action (2372), the system rotates the valve of stopcock (1100), position (2376), allowing the flow of saline from the IV bag to the patient, closing the sampling port (1900) and having the display mode (2374) indicate "Done".

Figure 26A:
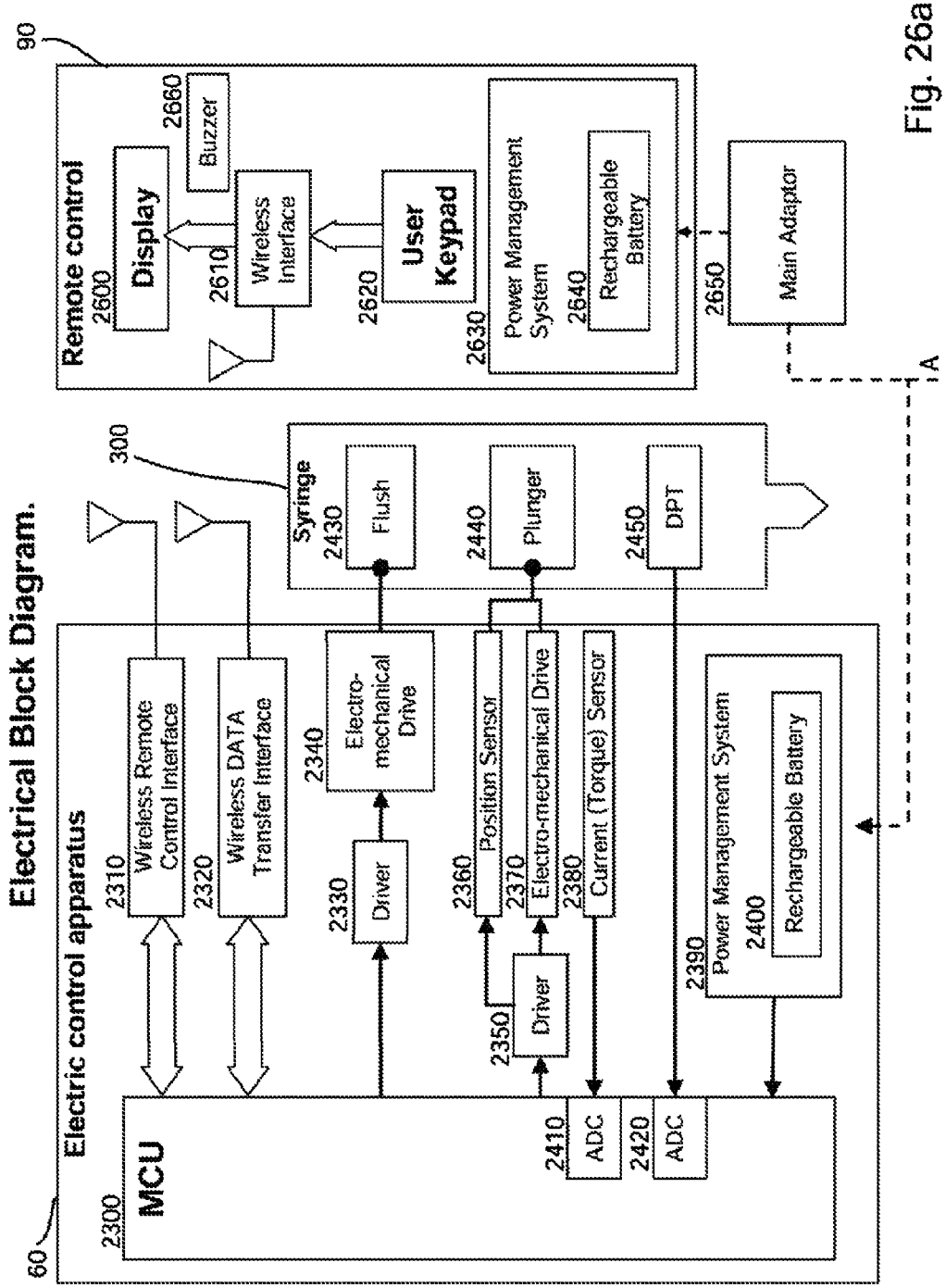
FIGS. 26a-b show schematically an electronic block diagram.
Figure 26B:
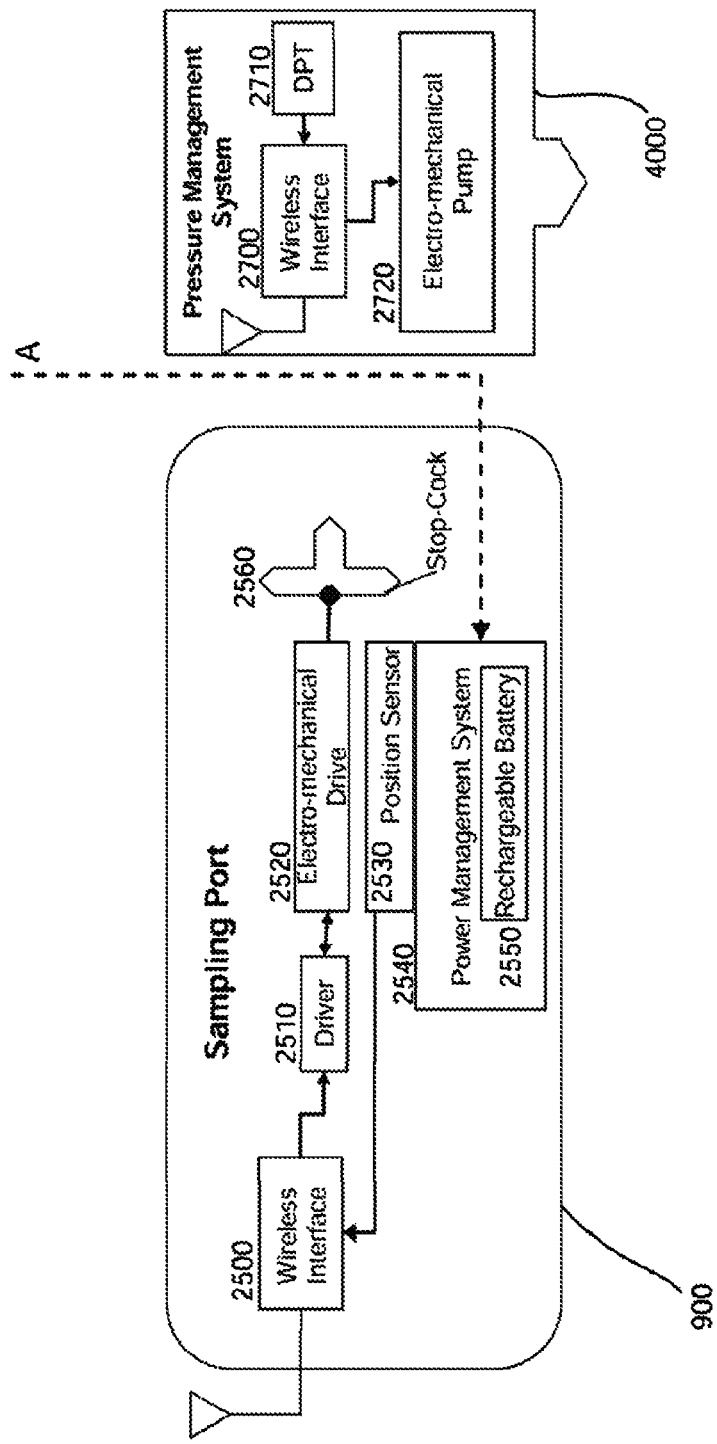

FIGS. 26a-b show the control schematic for the various mechanisms containing electronic inputs and outputs, particularly, the electronic apparatus (60), the syringe (300), the remote control (90), the sampling port mechanism (900) and the automatic pressure management system (4000). Calculations and control is governed by a microprocessor unit located in the electronic apparatus (60). Each remote subsystem can communicate by cable or by wireless transmission, and has a power management system containing a rechargeable battery power source. The electronic apparatus (60) has analogue to digital converters (ADC) for processing the various input signals (current sensors, pressure sensors, strain gauge etc.). The electronic apparatus (60) utilizes the current sensor, the position sensor, driver and electromechanical drive to power and control the plunger in syringe (300) and utilizes yet another driver and electromechanical drive to actuate the flush lever (2430) in the syringe (300). The remote control (90) has a display, buzzer and user keypad for user inputs. The sampling port mechanism (900) has a driver, position sensor and electromechanical drive to monitor and drive the position of valve (1100) according to commands sent by the electronic apparatus (60). Automatic pressure management system (4000) has an electro mechanical drive for its internal pump and a pressure transducer which can be located in the automatic pressure management system (4000) or by using the integrated pressure transducer in syringe (300).

Shown in FIG. 26a, the controller programming in electronic apparatus (60) can be customized for various designated usages, specifically the sequencing between sampling port mechanism (900) and syringe (300) can be arranged to accommodate various types of stopcock valves (1100) and user requirements. The controller programming can be adapted to any of the syringes described herein, regardless of the fluid channels in syringes (500, 600) remaining open during aspiration as oppose to the other syringes described.

The microprocessor computing unit (2300), or MCU, is a module capable of communicating with the modules within and without the electronic control apparatus (60), make calculations, convert analog signals to digital and vice-versa, and control of several types of timers and memories.

The wireless remote control interface module (2310) is capable of receiving and transmitting signals between the module (2610) of the remote control (90), the module (2700) of the pressure management system (4000), and the module (2500) of the sampling port (900). This said control interface module (2310) can also facilitate the communication between the MCU (2300) and external systems, such as the IT networks of the hospital, and can operate through infrared radio frequency or other type of frequencies.

The wireless data transfer interface module (2320) can be separated or unified with the remote control interface module (2310) to transmit data signals between the electric control apparatus (60), the remote control (90), the sampling port (900) and the pressure management system (4000).

The electro mechanical drive module (2340) can be a rotating motor, a linear actuator, or any other device that, through its functioning, opens and close the flush module (2340).

The driver module (2330) serves to convert, amplify and modulate signals originating from the microprocessor (2300) to enable control of the electro mechanical drive module (2340).

The flush module (2430), located in the syringe (300), is a flow restrictor that after receiving a mechanical input from the electromechanical drive (2340) and responsive thereto restricts or allows the flow of fluid.

The position sensor module (2360), which can be of an encoded type or another, is capable of sensing and recognizing the position of the plunger (2440) and transmitting this position via driver module (2350).

The driver module (2350) is capable of receiving instructions from the microprocessor computing unit (2300), in conjunction to the feedback that it receives from the current/torque sensor module (2380), in order to send control signals to the electro-mechanical drive module (2370), such that said drive module (2370) will move the plunger (2440) to the position required by the microprocessor computing unit (2300).

The current/torque sensor module (2380) is a torque sensor, or sensor of the current applied to the electro mechanical drive (2370), that could be of the strain gauge type, and is capable of "feeling" or measuring the torque applied to the electro mechanical drive (2370) by the resistance that the plunger (2440) offers to its rotation.

The power management system module (2390) controls the current supply to all the circuits of the electric control apparatus (60), besides controlling the charging of the rechargeable battery (2400).

The ADC module (2410), which is part of the microprocessor control unit (2300), receives the analog signals from the current/torque sensor module (2380), and transforms them into digital signals that can be read by the microprocessor control unit (2300).

The ADC module (2420), which is part of the microprocessor control unit (2300), receives the analog signals from the DPT module (2450) of syringe (300), and transforms them into digital signals that can be read by the microprocessor control unit (2300).

The remote control module (90), also seen in FIG. 26a, is a module that receives and transmits user data to the system, and includes a user interface for input.

The display module (2600) displays numbers, words and graphics of outputs and instructions.

The buzzer (2660) is a speaker that can emit alarm and confirmation sounds when energized by the MCU (2300).

The user keypad (2620) is an input keypad, which can be also of a touch-screen type, through which the user inputs instructions and data to the system.

The power management system module (2630) controls the current supply to all the circuits of the remote control (90), besides controlling the charging of the rechargeable battery (2640).

The wireless interface module (2610) is responsible for the communication between the remote control module (90) and the electric control apparatus (60), by transmitting and receiving signals from the wireless remote control interface module (2310) and the wireless data transfer interface module (2320).

Shown in FIG. 26b, the pressure management system module (4000) is the one that controls the pressure in the infusion bags, by controlling an electro-mechanical pump (2720) that inflates a pressure bag and receiving signals from a DPT (disposable pressure transducer) module (2710), which monitors the pressure inside the infusion bag. The data of the DPT module (2710) is transmitted by the wireless interface module (2700) to the wireless remote control interface module (2310) and the wireless data transfer interface module (2320) for analysis of the microprocessor computing unit (2300), which in turn, through the same means, sends control signals to the said electro-mechanical pump (2720), thus controlling the pressure in the infusion bags.

The sampling port module (900), also seen in FIG. 26b, is responsible for controlling the stopcock (2560).

The wireless interface module (2500) is the transmitter and receiver responsible for the communication between module (2500) and the electric control apparatus (60).

The driver (2510) receives instructions from the electric control apparatus (60) through the wireless interface module (2500), and send controls signals to the electro-mechanical drive (2520), which in turns moves the stopcock (2560) to the position required by the electric control apparatus (60)

The position sensor module (2530) "feels" the position of the stopcock (2560) and informs the electric control apparatus (60) of its position, through a feedback loop method, in order to verify and facilitate the control of the stopcock.

The power management system module (2540) controls the current supply to all the circuits of the sampling port (900), besides controlling the charging of the rechargeable battery (2550).

The main adaptor module (2650), shown in FIG. 26a, is a current recharger/adapter, whose function is the supply of electric current to the above mentioned modules (60), (90), (4000) and (900).

Although the invention has been shown and described in terms of specific embodiments, nevertheless changes and modifications will be evident to persons of ordinary skill in the art. Such changes and modifications that do not depart from the spirit and scope of the teachings herein are deemed to come within the purview of the claims.

What is claimed is:

1. An in-line sampling syringe for selectively introducing a fluid to and aspirating a fluid from a downstream fluid conduit connected to a catheterized patient, said syringe comprising:

a. a housing defining a closed system composed of a fluid chamber having a first opening into which fluid is aspirated and an air chamber having a second opening in which a relief element is positioned; b. a volume regulator mounted in said housing composed of a sealing gasket interposed between the fluid chamber and the air chamber and a drive mechanism connected to the sealing gasket for moving the sealing gasket for adjusting the volume of said fluid chamber; c. a rigid fluid line mounted in a fixed position in said housing through which fluid flows relative to a downstream fluid conduit via said first opening, said rigid fluid line passing through the sealing gasket in a slidably sealed manner, and said rigid fluid line terminating adjacent to said first opening; d. wherein said drive mechanism connected to the sealing gasket is mounted for linear sliding movement in said housing relative to said rigid fluid line; and e. a rotatably mounted control member, which can be operated manually single handedly, is operatively connected to said drive mechanism for: i. selectively controlling fluid flow relative to said rigid fluid line; and, ii. selectively linearly shifting said volume regulator relative to said housing to adjust the volume of said fluid chamber.

2. The syringe of claim 1 wherein the relief element is one of a filter and a resilient membrane.

3. The syringe of claim 2 wherein the filter has properties of one of antimicrobial and antibacterial.

4. The syringe of claim 1, wherein the drive mechanism is a rack and pinion mechanism.

5. The syringe of claim 4, further including a shaft mounted for pivoting that is coupled with one end of an elongated handle the other end of the elongated handle being free, said shaft being coupled to rotate said pinion of said rack and pinion mechanism, said elongated handle being rotatable single-handedly.

6. The syringe of claim 5 wherein a scale marked with indicia is mounted on the housing and the free end of said elongated handle defines a pointer that coacts with the indicia on the scale to show precise correlated volume of aspirated fluid.

7. The syringe of claim 1, wherein the rigid fluid line comprises a first end in communication the fluid chamber and a second end in communication with a third opening to said housing.

8. The syringe of claim 1 further including a pressure transducer operatively mounted relative to said housing to sense pressure in one of said rigid fluid line and the first opening to said housing whereby an occlusion affecting the downstream fluid conduit connected to a catheterized patient can be sensed and detected; detection circuitry operatively connected to receive pressure signals from said pressure transducer and in response thereto to signal detection of an occlusion by at least one of a display and audible alarm activated response.

9. The syringe of claim 8 further including a zeroing arrangement for the pressure transducer.

10. The syringe of claim 1 wherein the rotatably mounted control member includes a holding mechanism for detachably holding the rotatably mounted control member in a preselected position.

11. The syringe of claim 1 wherein one end of the termination of the rigid fluid line adjacent to said first opening is embedded in the housing at the first opening, for stability, with channels formed in the housing surrounding the embedded terminal end to enable fluid to flow from the first opening around the embedded terminal end into the housing.

12. In combination an in-line sampling system for selectively introducing a fluid to and aspirating a fluid from a downstream fluid conduit connected to a catheterized patient, comprising: the syringe of claim 1; a sampling port having a stopcock valve having a first port for connecting to a downstream fluid conduit connected to a catheterized patient, a second port connected to a sampling site for sampling and a third porter with the syringe according to claim 1 having its first opening via a downstream fluid conduit connected to the third port of the stopcock valve; said rigid fluid line mounted in a fixed position in the housing of the syringe being connectable to a flushing fluid supply; a controlling pressurizing mechanism for applying pressure to the flushing fluid supply; a motor connected to the stopcock valve to control its position; and an electronic controller operatively controlling said motor to position the stopcock valve to effect a monitoring step; a flushing step, an aspirating step and a sampling step.

13. The combination according to claim 12 further including a pressure measuring mechanism for monitoring fluid pressure in said in-line sampling system.

14. The combination according to claim 12 wherein the electronic controller is operative for controlling monitoring of the patient blood pressure through the in-line sampling system, aspirating blood from a patient to the sampling valve for blood sampling and flushing fluid from the syringe back to the patient.

15. The combination according to claim 14 wherein the electronic controller includes one motor operatively coupled to the syringe, a second motor operatively coupled to the stopcock valve with the electronic controller automatically synchronizing the stopcock valve of the sampling port with the syringe, and automatically stepping through a monitoring operation, an aspirating operation, a sampling operation and a flushing operation.

16. The combination according to claim 12 wherein the pressurizing mechanism for applying pressure to a flushing fluid supply-includes a pressure cuff and a pump to apply pressure to the cuff and a valve to relieve pressure from the cuff.

17. The combination according to claim 12 further including a pressure transducer to monitor the pressure of fluid inside the system to provide an indication of the patient blood pressure.

* * * * *